United States Patent [19]
Sidransky

[11] Patent Number: 6,025,127
[45] Date of Patent: Feb. 15, 2000

[54] NUCLEIC ACID MUTATION DETECTION IN HISTOLOGIC TISSUE

[75] Inventor: David Sidransky, Baltimore, Md.

[73] Assignee: The Johns Hopkins University School of Medicine, Baltimore, Md.

[21] Appl. No.: 08/181,664

[22] Filed: Jan. 14, 1994

[51] Int. Cl.[7] .................................................. C12Q 1/68
[52] U.S. Cl. .......................... 435/6; 536/23.1; 536/23.5
[58] Field of Search ........................ 436/6, 91.2, 172.3; 536/24.31, 23.1, 23.5; 514/44; 800/2

[56] References Cited

U.S. PATENT DOCUMENTS

| | | | |
|---|---|---|---|
| 4,683,195 | 7/1987 | Mullis et al. | 435/6 |
| 5,141,813 | 8/1992 | Nelson | 428/402 |
| 5,248,671 | 9/1993 | Smith | 514/44 |
| 5,582,986 | 12/1996 | Monia et al. | 435/6 |

OTHER PUBLICATIONS

Maryalica Stetier–Steveson et al., "Detection of Occult Follicular Lymphoma by Specific DNA & Amplification", *Blood*, vol. 72, No. 8 (Nov. 1989), pp. 1622–1625.

Takashi Deguchi et al., "Detection of Micrometastatic Prostate Cancer Cells in Lymph Nodes by Reverse Transcriptase– Polymerase Chain Reaction", *Cancer Research*, vol. 53, pp. 5350–5354 (Nov. 15, 1993).

Hodgson, Bio/Technology 13: 222 (Mar. 1995).
Sidransky et al, Science 252: 706 (1991).
Stratagene 1992 Product Catalog, p. 75.
Uhlmann et al, Chemical Reviews 90(4), 543 (1990).
Molecular Biology and Biotechnology, Third Edition, Walker et al (ed.), 1993, Royal Society of Chemistry, Cambridge, UK, pp. 172–173.
Friedmann, Cancer Supplement 70: 1810 (1992).
Wallace et al, Methods Enzymol. 152: 432 (1987).
Harlow et al, Molec. Cell. Biol. 5: 1601 (1985).
Gura, Science 270: 575 (1995).
Rojanasakul, Adv. Drug Delivery Rev. 18: 115 (1996).
Orkin et al, Report and Recommendations of the Panel to Assess the NIH Investment in Research on Gene Therapy, Dec. 7, 1995.

*Primary Examiner*—James Martinelli
*Attorney, Agent, or Firm*—Gray, Cary, Ware & Freidenrich, LLP; Lisa A. Haile

[57] ABSTRACT

Methods are provided for detection of target neoplastic nucleic acids in a tissue specimen, including a tumor margin or lymph node, and reagents therefor, wherein the nucleic acids are preferably mutant tumor suppressor genes or proto oncogenes. Methods for treatment of cell proliferative diseases utilizing ribozymes or antisense oligonucleotides specific for the target mutant nucleic acids and/or replacement wild type genes are also disclosed.

20 Claims, 9 Drawing Sheets

SEQUENCE LISTING (1) GENERAL INFORMATION:

(iii) NUMBER OF SEQUENCES: 82

(2) INFORMATION FOR SEQ ID NO:1:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (genomic)

(ix) FEATURE:
             (A) NAME/KEY: CDS
             (B) LOCATION: 1..26

(xi) SEQUENCE DESCRIPTION: SEQ ID NO:1:

AAGTCAGGGC ACAAGTGAAT TCCTAC                                           26

(2) INFORMATION FOR SEQ ID NO:2:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 1..27

(xi) SEQUENCE DESCRIPTION: SEQ ID NO:2:

AAGGGTGGTT GTCAGTGGAA TTCGATG                                          27

(2) INFORMATION FOR SEQ ID NO:3:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 1..27

(xi) SEQUENCE DESCRIPTION: SEQ ID NO:3:

GAGGCCAGTG CGCCTTGGAA TTCCTAC                                          27

(2) INFORMATION FOR SEQ ID NO:4:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 1..26

(xi) SEQUENCE DESCRIPTION: SEQ ID NO:4:

GCGGTGGAGG AGACGAAGAA TTCAGT                                           26

(2) INFORMATION FOR SEQ ID NO:5:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: DNA (genomic)

(ix) FEATURE:
            (A) NAME/KEY: CDS
            (B) LOCATION: 1..19

(xi) SEQUENCE DESCRIPTION: SEQ ID NO:5:

TTCACTTGTG CCCTGACTT                                                    19

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..20

(xi) SEQUENCE DESCRIPTION: SEQ ID NO:6:

CTGGAAACTT TCCACTTGAT                                                   20

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..18

(xi) SEQUENCE DESCRIPTION: SEQ ID NO:7:

CCACTGACAA CCACCCTT                                                     18

(2) INFORMATION FOR SEQ ID NO:8:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..18

(xi) SEQUENCE DESCRIPTION: SEQ ID NO:8:

CCAAGGCGCA CTGGCCTC                                                     18

(2) INFORMATION FOR SEQ ID NO:9:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..18

(xi) SEQUENCE DESCRIPTION: SEQ ID NO:9:

CACAAACATG CACCTCAA                                         18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:10:

TCTCCCAGTA CAGGCACA                                         18

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:11:

TGCGCCGGCC TCTCCCA                                          17

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:12:

CCGGTTCATG GCGCCCAT                                         18

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..27

(xi) SEQUENCE DESCRIPTION: SEQ ID NO:13:

```
GTAGGAATTC ACTTGTGCCC TGACTTG                                              27

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..29

(xi) SEQUENCE DESCRIPTION: SEQ ID NO:14:

CATCGAATTC TGGAAACTTT CCACTTGAT                                            29

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:15:

CCTGCAGTAG TCCCCTG                                                         17

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:16:

CCTCAACAGG ATGTTTTG                                                        18

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:17:

GCAGCTGTGA GTTGATTC                                                        18
```

(2) INFORMATION FOR SEQ ID NO:18:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..16

(xi) SEQUENCE DESCRIPTION: SEQ ID NO:18:

GCCCGGCCCC CGCGTC                                                         16

(2) INFORMATION FOR SEQ ID NO:19:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..16

(xi) SEQUENCE DESCRIPTION: SEQ ID NO:19:

CCGCGTCTGC GCCATG                                                         16

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:20:

GGCCATCCAC AAGCAGT                                                        17

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:21:

ACAGCACACG ACGGAGG                                                        17

(2) INFORMATION FOR SEQ ID NO:22:

(i) SEQUENCE CHARACTERISTICS:

(A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:22:

CGGAGGTTCT GAGGCGC                                                17

(2) INFORMATION FOR SEQ ID NO:23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:23:

TTGTGAGGCA CTGCCCC                                                17

(2) INFORMATION FOR SEQ ID NO:24:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..16

(xi) SEQUENCE DESCRIPTION: SEQ ID NO:24:

AGGCGCTTCC CCCACC                                                 16

(2) INFORMATION FOR SEQ ID NO:25:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..16

(xi) SEQUENCE DESCRIPTION: SEQ ID NO:25:

CCCCACCGTG AGCGCT                                                 16

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: single (D) TOPOLOGY: linear (ii) MOLECULE TYPE: DNA (genomic)

(ix) FEATURE:
        (A) NAME/KEY: CDS
        (B) LOCATION: 1..19

(xi) SEQUENCE DESCRIPTION: SEQ ID NO:26:

ATCCGAGTGA AAGGAAATT                                                    19

(2) INFORMATION FOR SEQ ID NO:27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..19

(xi) SEQUENCE DESCRIPTION: SEQ ID NO:27:

TGTGGAAGTC TTTGGATGA                                                    19

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:28:

TGTGGAGGAT TTGGATGA                                                     18

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:29:

TGTGGAGTGT TTGGATGA                                                     18

(2) INFORMATION FOR SEQ ID NO:30:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
            (A) NAME/KEY: CDS
            (B) LOCATION: 1..19

(xi) SEQUENCE DESCRIPTION: SEQ ID NO:30:

ACACTTTTTG ACATAGTGT                                                19

(2) INFORMATION FOR SEQ ID NO:31:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..16

(xi) SEQUENCE DESCRIPTION: SEQ ID NO:31:

CCCCACCTTG AGCGCT                                                   16

(2) INFORMATION FOR SEQ ID NO:32:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..18

(xi) SEQUENCE DESCRIPTION: SEQ ID NO:32:

ACATAGTATG GTGGTGCC                                                 18

(2) INFORMATION FOR SEQ ID NO:33:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..18

(xi) SEQUENCE DESCRIPTION: SEQ ID NO:33:

ACATAGTTTT GTGGTGCC                                                 18

(2) INFORMATION FOR SEQ ID NO:34:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS (B) LOCATION: 1..16

(xi) SEQUENCE DESCRIPTION: SEQ ID NO:34:

GGTGCCCTGT GAGCCG                                                        16

(2) INFORMATION FOR SEQ ID NO:35:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..16

(xi) SEQUENCE DESCRIPTION: SEQ ID NO:35:

GGTGCCCCAT GAGCCG                                                        16

(2) INFORMATION FOR SEQ ID NO:36:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..16

(xi) SEQUENCE DESCRIPTION: SEQ ID NO:36:

GGTGCCCTCT GAGCCG                                                        16

(2) INFORMATION FOR SEQ ID NO:37:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:37:

TGGCTCTGAG TGTACCAC                                                      18

(2) INFORMATION FOR SEQ ID NO:38:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:38:

```
CATCCACTGC AACTACAT                                                    18

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..20

(xi) SEQUENCE DESCRIPTION: SEQ ID NO:39:

CTACAACTAA ATGTGTAACA                                                  20

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..20

(xi) SEQUENCE DESCRIPTION: SEQ ID NO:40:

CAACTACATT TGTAACAGTT                                                  20

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..20

(xi) SEQUENCE DESCRIPTION: SEQ ID NO:41:

CAACTACATA TGTAACAGTT                                                  20

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..20

(xi) SEQUENCE DESCRIPTION: SEQ ID NO:42:

ACTACATGTT TAACAGTTCC                                                  20
```

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..20

(xi) SEQUENCE DESCRIPTION: SEQ ID NO:43:

ACTACATGTA TAACAGTTCC                                                20

(2) INFORMATION FOR SEQ ID NO:44:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:44:

CAGTTCCTTC ATGGGCG                                                  17

(2) INFORMATION FOR SEQ ID NO:45:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:45:

GCATGGGCGT TATGAAC                                                  17

(2) INFORMATION FOR SEQ ID NO:46:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:46:

GCATGGGCTG CATGAAC                                                  17

(2) INFORMATION FOR SEQ ID NO:47:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:47:

GCATGGGCGA CATGAAC                                                            17

(2) INFORMATION FOR SEQ ID NO:48:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:48:

GGCGGCTTGA ACCGGAG                                                            17

(2) INFORMATION FOR SEQ ID NO:49:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:49:

CATGAACCTG AGGCCCAT                                                           18

(2) INFORMATION FOR SEQ ID NO:50:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:50:

GCATGAACTG GAGGCCCA                                                           18

(2) INFORMATION FOR SEQ ID NO:51:

(i) SEQUENCE CHARACTERISTICS:
        (A) LENGTH: 18 base pairs
        (B) TYPE: nucleic acid

```
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:51:

GCATGAACCA GAGGCCCA                                                    18

(2) INFORMATION FOR SEQ ID NO:52:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:52:

AACCGGAGTC CCATCCTC                                                    18

(2) INFORMATION FOR SEQ ID NO:53:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..16

(xi) SEQUENCE DESCRIPTION: SEQ ID NO:53:

GAACCGGGGG CCCATC                                                      16

(2) INFORMATION FOR SEQ ID NO:54:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:54:

GAGGCCCAAC CTCACCA                                                     17

(2) INFORMATION FOR SEQ ID NO:55:

(i) SEQUENCE CHARACTERISTICS:
        (A) LENGTH: 17 base pairs
        (B) TYPE: nucleic acid
        (C) STRANDEDNESS: single
        (D) TOPOLOGY: linear
```

(ii) MOLECULE TYPE: DNA (genomic)

(ix) FEATURE:
              (A) NAME/KEY: CDS
              (B) LOCATION: 1..17

(xi) SEQUENCE DESCRIPTION: SEQ ID NO:55:

CATCACACCG GAAGACT                                                            17

(2) INFORMATION FOR SEQ ID NO:56:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY: CDS
              (B) LOCATION: 1..18

(xi) SEQUENCE DESCRIPTION: SEQ ID NO:56:

TCTACTGGAA CGGAACAG                                                           18

(2) INFORMATION FOR SEQ ID NO:57:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY: CDS
              (B) LOCATION: 1..18

(xi) SEQUENCE DESCRIPTION: SEQ ID NO:57:

TTGAGGTGCA TGTTTGTG                                                           18

(2) INFORMATION FOR SEQ ID NO:58:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY: CDS
              (B) LOCATION: 1..18

(xi) SEQUENCE DESCRIPTION: SEQ ID NO:58:

TTGAGGTGGG TGTTTGTG                                                           18

(2) INFORMATION FOR SEQ ID NO:59:

(i) SEQUENCE CHARACTERISTICS:
              (A) LENGTH: 17 base pairs
              (B) TYPE: nucleic acid
              (C) STRANDEDNESS: single
              (D) TOPOLOGY: linear (ii) MOLECULE TYPE: DNA (genomic)

(ix) FEATURE:

(A) NAME/KEY: CDS
            (B) LOCATION: 1..17

(xi) SEQUENCE DESCRIPTION: SEQ ID NO:59:

GCTGTTTATG CCTGCCT                                                        17

(2) INFORMATION FOR SEQ ID NO:60:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..18

(xi) SEQUENCE DESCRIPTION: SEQ ID NO:60:

TGCCTGTACT GGGAGAGA                                                       18

(2) INFORMATION FOR SEQ ID NO:61:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..18

(xi) SEQUENCE DESCRIPTION: SEQ ID NO:61:

TGCCTGTTCT GGGAGAGA                                                       18

(2) INFORMATION FOR SEQ ID NO:62:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..18

(xi) SEQUENCE DESCRIPTION: SEQ ID NO:62:

TGCCTGTCGT GGGAGAGA                                                       18

(2) INFORMATION FOR SEQ ID NO:63:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..17

(xi) SEQUENCE DESCRIPTION: SEQ ID NO:63:

CTGTCCTGAG AGAGACC                                                17

(2) INFORMATION FOR SEQ ID NO:64:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: CDS
         (B) LOCATION: 1..17

(xi) SEQUENCE DESCRIPTION: SEQ ID NO:64:

CTGTCCTGGG GAGAGAC                                                17

(2) INFORMATION FOR SEQ ID NO:65:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: CDS
         (B) LOCATION: 1..17

(xi) SEQUENCE DESCRIPTION: SEQ ID NO:65:

TGGGAGACAC CGGCGCA                                                17

(2) INFORMATION FOR SEQ ID NO:66:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: CDS
         (B) LOCATION: 1..17

(xi) SEQUENCE DESCRIPTION: SEQ ID NO:66:

TGGGAGAGAG CGGCGCA                                                17

(2) INFORMATION FOR SEQ ID NO:67:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: CDS
         (B) LOCATION: 1..18

(xi) SEQUENCE DESCRIPTION: SEQ ID NO:67:

GCGCACAAAG GAAGAGAA                                               18

(2) INFORMATION FOR SEQ ID NO:68:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..19

(xi) SEQUENCE DESCRIPTION: SEQ ID NO:68:

GCACAGAGAA AGAGAATCT                                                    19

(2) INFORMATION FOR SEQ ID NO:69:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:69:

GAAAGGGTAG CCTCACC                                                      17

(2) INFORMATION FOR SEQ ID NO:70:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:70:

GAGCCTCCCC ACGAGCT                                                      17

(2) INFORMATION FOR SEQ ID NO:71:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:71:

CTCACCACTA GCTGCCC                                                      17

(2) INFORMATION FOR SEQ ID NO:72:

```
        (i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 1..17

(xi) SEQUENCE DESCRIPTION: SEQ ID NO:72:

CTCACCACGC ACTGCCC                                                  17

(2) INFORMATION FOR SEQ ID NO:73:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 1..17

(xi) SEQUENCE DESCRIPTION: SEQ ID NO:73:

GGTGCGTATT TGTGCCT                                                  17

(2) INFORMATION FOR SEQ ID NO:74:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 1..18

(xi) SEQUENCE DESCRIPTION: SEQ ID NO:74:

TGTGCCTGTA CTGGGAGA                                                 18

(2) INFORMATION FOR SEQ ID NO:75:

(i) SEQUENCE CHARACTERISTICS:
             (A) LENGTH: 16 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 1..16

(xi) SEQUENCE DESCRIPTION: SEQ ID NO:75:

TGGGAGACAC CGGCGC                                                   16

(2) INFORMATION FOR SEQ ID NO:76:

(i) SEQUENCE CHARACTERISTICS:
             (A) LENGTH: 31 base pairs
```

(B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..31

(xi) SEQUENCE DESCRIPTION: SEQ ID NO:76:

CAUCAUCAUC AUTTCACTTG TGCCCTGACT T                               31

(2) INFORMATION FOR SEQ ID NO:77:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..32

(xi) SEQUENCE DESCRIPTION: SEQ ID NO:77:

CAUCAUCUAC UACTGGAAAC TTTCCACTTG AT                              32

(2) INFORMATION FOR SEQ ID NO:78:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..30

(xi) SEQUENCE DESCRIPTION: SEQ ID NO:78:

CUACUACUAC UACCACTGAC AACCACCCTT                                 30

(2) INFORMATION FOR SEQ ID NO:79:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..30

(xi) SEQUENCE DESCRIPTION: SEQ ID NO:79:

CAUCAUCAUC AUCCAAGGCG CACTGGCCTC                                 30

(2) INFORMATION FOR SEQ ID NO:80:

(i) SEQUENCE CHARACTERISTICS:
        (A) LENGTH: 17 base pairs
        (B) TYPE: nucleic acid
        (C) STRANDEDNESS: single
        (D) TOPOLOGY: linear -continued (ii) MOLECULE TYPE: DNA (genomic)

(ix) FEATURE:
    (A) NAME/KEY: CDS
    (B) LOCATION: 1..17

(xi) SEQUENCE DESCRIPTION: SEQ ID NO:80:

TGGGAGAGGC CGGCGCA                                              17

(2) INFORMATION FOR SEQ ID NO:81:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:81:

ATGGGCGCCA TGAACCGG                                             18

(2) INFORMATION FOR SEQ ID NO:82:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:82:

TGTGCCTGTA CTGGGAGA                                             18

NUCLEIC ACID MUTATION DETECTION IN HISTOLOGIC TISSUE

BACKGROUND OF THE INVENTION

1. Field of the Invention

This invention relates to a method of detecting a target neoplastic nucleic acid in histologic tissue external to a primary neoplasm, and reagents useful therein.

2. Description of Related Art

An increasing body of evidence implicates somatic mutations as causally important in the induction of human cancers. These somatic mutations may accumulate in the genomes of previously normal cells, some of which may then demonstrate the phenotypes associated with malignant growth. Such oncogenic mutations may include a number of different types of alterations in DNA structure, including deletions, translocations and single nucleotide alterations. The latter, also known as point mutations, may frequently intervene in carcinogenesis, since a variety of mutagenic chemicals induce such mutations. In addition, such mutations may occur spontaneously as a result of mistakes in DNA replication.

Advances in recombinant DNA technology have led to the discovery of normal cellular genes (proto-oncogenes and tumor suppressor genes) that control growth, development, and differentiation. Under certain circumstances, the regulation of these genes is altered, causing normal cells to assume neoplastic growth behavior. There are over 40 known proto-oncogenes and suppressor genes to date, which fall into various categories depending on their functional characteristics. These include, (1) growth factors and growth factor receptors, (2) messengers of intracellular signal transduction pathways, for example, between the cytoplasm and the nucleus, and (3) regulatory proteins influencing gene expression and DNA replication.

Point mutations have been directly implicated in the causation of many human tumors. Some tumors carry oncogenes of the ras gene family, which differ from their normal cellular counterpart proto-oncogenes by the presence of a point mutation at one of a limited number of sites in these genes. Similarly, point mutations in critical regions of tumor suppressor genes, such as p53, are often detected in tumor cells. Mutation of the p53 suppressor gene is the most common alteration seen in epithelial tumors and, indeed, in all human tumors (Hollstein, M. et al., Science 253:49–53, 1991).

When a tumor suppressor gene, such as p53, becomes mutated, cell proliferation accelerates in the absence of the suppressor. On the other hand, mutations in proto-oncogenes that transform them to active oncogenes, such as a mutant ras oncogene, produces cell proliferation caused by presence of the mutant gene itself. These mutations represent qualitative changes in the tumor cell genome that distinguish these cells from normal cells and provide a basis for diagnosis of the genetic origin of a tumor under study.

Identification of the mutations that have created active oncogenes may provide important diagnostic and prognostic clues for tumor development. For example, a number of mutations have been found to alter the 12th codon of the ras oncogenes, causing replacement of a normally present glycine by any of a number of alternative amino acid residues. Such amino acid substitutions create a potent transforming allele. Thus, the presence of a particular nucleotide substitution may be a strong determinant of the behavior of the tumor cell (e.g., its rate of growth, invasiveness, etc.). As a result, nucleotide hybridization probes of oncogene mutations have promise as diagnostic reagents in clinical oncology.

Head and neck squamous carcinoma, commonly associated with mutant p53, kills over 11,000 Americans each year, yet little is known concerning the genetic events involved in progression of these malignancies. A number of neoplasms found in the gastrointestinal tract, especially colorectal cancer, are better understood and commonly associated with oncogene mutations. Colorectal cancer is the third most common malignancy in the world, with 570,000 new cases expected each year. Treatment of all cancers depends on the tumor stage as determined by clinical evaluation and surgical resection. The standard technique for assessing the spread of a tumor is surgical resection of a primary tumor followed by careful review using light microscopy of surgical margins and other tissue, including lymph nodes. Under existing procedure, the adjacent tissue is stained by standard techniques and assessed under light microscopy for the presence of tumor cells. Accurate therapeutic staging assesses the extent of tumor spread locally as well as the presence of regional metastases in more distant sites, such as lymph nodes. Accurate histopathologic assessment is critical since it provides important prognostic indicators that determine the probability of survival for a given patient following surgical resection of the primary tumor.

Despite many years of research and billions of dollars in expenditures the long term survival of patients with malignancies remains disappointedly low, even where no tumor cells were detected in the tumor margins or more distant tissues. This inability to more accurately stage such patients might be due to the limitation inherent is the standard histopathologic methodology which is based upon visual observation and morphologic assessment under light microscopy of adjacent tissue and regional lymph nodes. Thus, a method which uses a more precise technique capable of determining spread of the disease at an earlier stage might provide a more accurate indication of the extent of tumor metastases into adjacent and regional tissues. The present invention provides such a method.

SUMMARY OF THE INVENTION

The present invention arose from the unexpected finding that nucleic acid having a mutant nucleotide sequence associated with a primary tumor is detectable in the adjacent histopathologic surgical margins and more distant tissues, such as regional lymph nodes, which are apparently "normal" when examined by standard histological techniques. The invention accomplishes this greatly improved accuracy by application of precise molecular techniques.

As a consequence of this discovery, the present invention represents a significant advance over such standard medical techniques as visual, light microscopy tissue biopsy and morphologic assessment of such tissue, by providing a rapid, and accurate molecular biologic method for detecting at the molecular level mutant nucleotide sequences associated with a primary tumor. The approach of the invention is based upon DNA amplification and can identify as few as a single cell carrying a mutant gene among a large excess (greater than 10,000) of normal cells. Based on this finding, it is now possible to detect target nucleic acids from cells previously associated with a large number of disease states which are present in tissue that appears normal.

The present invention provides a method which can be used as an adjunct to cytopathology, to screen high-risk populations and to monitor high risk patients undergoing chemoprevention or chemotherapy.

DESCRIPTION OF THE DRAWINGS

FIG. 7 shows a molecular anlaysis of surgical margins and lymph nodes. Autoradiographs of plaque lifts hybridized with mutant-specific oligomers derived from each patient's tumor are shown. Positive (specific) hybridizing clones (black dots) are detected in surgical margins (M), in lymph nodes (L), and in the primary tumor (T) as a positive control. Details of each patient in FIGS. 7A, B, and C, and percentage of tumor cells in margins and lymph nodes appear in Tables 7, 8, and 9.

DETAILED DESCRIPTION OF THE INVENTION

Figure 1:
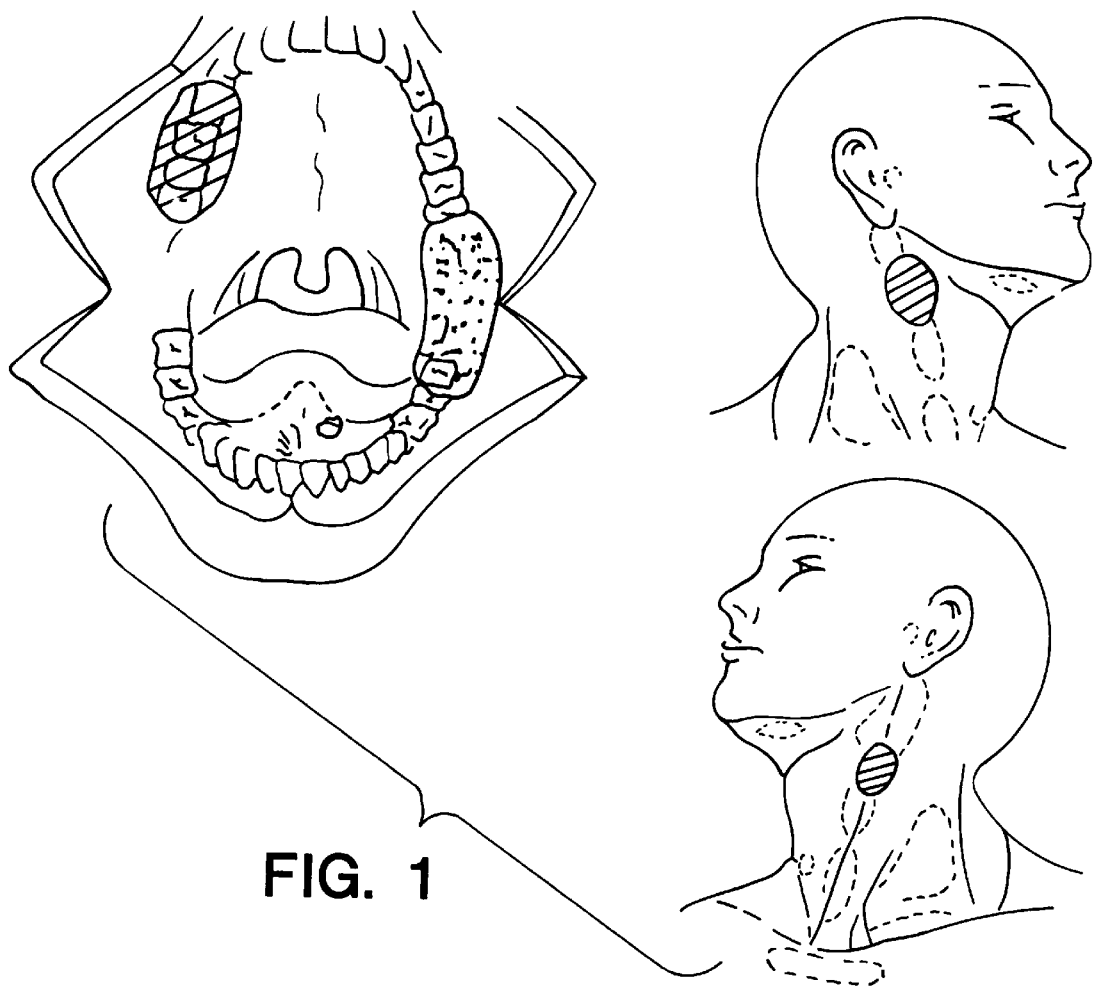
FIG. 1 is a tumor map showing physical findings at initial presentation. Right alveolar ridge (ALV) lesion—cross-hatching; left retromolar trigone lesion (RMT)—stippling. Floor of mouth (FOM) leukoplakia—open circle. Bilateral clinically apparent neck masses are cross-hatched to indicate precise biological linkage to ALV.

The present invention relates to a method of detecting a neoplastic nucleic acid having a mutant nucleotide sequence present in a histopathologic tissue sample external to a primary neoplasm, such as a tumor margin specimen, comprising isolating the nucleic acid present in the specimen and detecting the presence of the neoplastic target nucleic acid wherein the presence of the nucleic acid sequence is known to be associated with neoplasia, such as, neoplasia of the head or neck.

The term "neoplastic" nucleic acid refers to a nucleic acid sequence which directly or indirectly is associated with or causes a neoplasm. As used herein the term "tumor margin" refers to the tissue surrounding a discernible tumor. In the case of surgical removal of a solid tumor, the tumor margin is the tissue cut away with the discernible tumor that usually appears to be normal to the naked eye. More particularly, as used herein, "margin" refers to the edge, border or boundary of a tumor. The margin generally extends from about 1 mm to about 4 mm from the primary tumor but can be greater depending upon the size of the primary solid tumor. The term "regional lymph node" refers to lymphoid tissue forming lymphoid organs or nodes which are in close proximity to the primary tumor. For example, regional lymph nodes in the case of head and neck carcinomas include cervical lymph nodes, prelaryngeal lymph nodes, pulmonary juxtaesophageal lymph nodes and submandibular lymph nodes. Regional lymph nodes for mammary tissue carcinomas include the axillary and intercostal nodes. The term "external to a primary neoplasm" means that the specimen is taken from a site other than directly from the primary neoplasm itself.

In its broadest sense, the present invention allows the detection of any neoplastic target nucleic acid sequence of diagnostic or therapeutic relevance, where the target nucleic acid sequence is present in a tissue sample such as that heretofore subjected to histopathologic examination using techniques of light microscopy, such as the margins of a primary tumor or a regional lymph node. Thus, the target nucleotide sequence may be, for example, a mutant nucleotide, a restriction fragment length polymorphism (RFLP), a nucleotide deletion, a nucleotide substitution, or any other mammalian nucleic acid sequence of interest in such tissue specimens. As used herein the term "mutant or mutated" as applied to a target neoplastic nucleotide sequence shall be understood to encompass a mutation, a restriction fragment length polymorphism, a nucleic acid deletion, or a nucleic acid substitution.

In one embodiment, the method of the invention is applicable to detection of mutant nucleotide sequences associated with benign as well as malignant neoplasias and tumors. In a preferred embodiment, neoplasia of the head or neck, is detected, although the method can be used to detect any neoplastic mutant nucleotide sequence, regardless of origin, as long as the sequence is detectably present in a histologic specimen. For example, neoplasia of regional lymph nodes associated with a primary mammary tumor can be detected utilizing the method of the invention. The specimen can also be chyle or blood.

Numerous nucleic acids having mutant nucleotide sequences that produce an abnormal gene product are known to be associated with various neoplasias. Among the most common mutant nucleotide sequences are those occurring in oncogenes and tumor suppressor genes, such as mutations of p53 and K-ras. Of special significance in the present invention is the detection of mutations of the p53 tumor suppressor gene (Vogelstein, *Nature*, 3:681, 1990).

Nearly 100 oncogenes have been identified. Though the number of known tumor suppressor genes is far less, the number is growing rapidly. Some of the known or candidate tumor suppressor genes and the neoplasias with which they are associated (J. Marx, *Science*, 261:1385–1367, 1993) are shown in Table 1 below.

TABLE 1

| GENE | CANCER TYPE | HEREDITARY SYNDROME |
| --- | --- | --- |
| APC | Colon Carcinoma | Familiar adenomatous polyposis |
| DCC | Colon Carcinoma | — |
| NF1 | Neurofibromas | Neurofibromatosis type 1 |
| NF2 | Schwannomas and meningiomas | Neurofibromatosis type 2 |
| p53 | 50% of all cancers | |
| Rb | Retinoblastoma | Retinoblastoma |
| RET | Thyroid carcinoma; pheochromocytoma | Multiple endocrine neoplasia type 2 |
| VHL | Kidney carcinoma | von Hippel-Lindau disease |
| WT-1 | Nephroblastoma | Wilms tumor |

When it is desired to amplify the target nucleotide sequence before detection, such as a mutant nucleotide sequence, this can be accomplished using oligonucleotide(s) that are primers for amplification. These unique oligonucleotide primers are based upon identification of the flanking regions contiguous with the mutant nucleotide sequence. For example, in the case of p53, these oligonucleotide primers comprise sequences which are capable of hybridizing with nucleotide sequences flanking the loci of mutations, such as the following p53 nucleotide sequences:

a) 5'-AAGTCAGGGCACAAGTGAATTCCTAC-3' (SEQUENCE ID NO. 1) and
b) 5'-AAGGGTGGTTGTCAGTGGAATTCGATG-3' (SEQUENCE ID NO.2) for exons 5–6;
c) 5'-GAGGCCAGTGCGCCTTGGMTTCCTAC-3' (SEQUENCE ID NO. 3) and
d) 5'-GCGGTGGAGGAGACGMGMATCAGT-3' (SEQUENCE ID NO. 4) for exons 7–8.
e) sequences complementary to a.) through d.).

Primers that hybridize to these flanking sequences are, for example, the following:

a) 5'-TTCACTTGTGCCCTGACTT-3' (SEQUENCE ID NO. 5);
b) 5'-CTGGAAACTTTCCACTTGAT-3' (SEQUENCE ID NO. 6);
c) 5'-CCACTGACMCCACCCTT-3' (SEQUENCE ID NO. 7);
d) 5'-CCMGGCGCACTGGCCTC-3' (SEQUENCE ID NO. 8); and
e) sequences complementary to a.) through d.).

One skilled in the art will be able to generate primers suitable for amplifying target sequences of additional genes, such as those flanking loci of known mutations in proto-oncogenes and tumor suppressor genes, using routine skills known in the art and the teachings of this invention.

In general, the primers used according to the method of the invention embrace oligonucleotides of sufficient length and appropriate sequence which provides specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product that is substantially complementary to a target nucleic acid strand. The oligonucleotide primer typically contains 15–22 or more nucleotides, although it may contain fewer nucleotides as long as the primer is of sufficient specificity to allow essentially only the amplification of the specifically desired target nucleotide sequence (i.e., the primer is substantially complementary).

Experimental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, Including temperature, buffer, and nucleotide composition.

Primers used according to the method of the invention are designed to be "substantially" complementary to each strand of mutant nucleotide sequence to be amplified. Substantially complementary means that the primers must be sufficiently complementary to hybridize with their respective strands under conditions which allow the agent for polymerization to function. In other words, the primers should have sufficient complementarily with the flanking sequences to hybridize therewith and permit amplification of the mutant nucleotide sequence. Preferably, the 3' terminus of the primer that is extended has perfectly base paired complementarity with the complementary flanking strand.

Oligonucleotide primers used according to the invention are employed in any amplification process that produces increased quantities of target nucleic acid. Typically, one primer is complementary to the negative (−) strand of the mutant nucleotide sequence and the other is complementary to the positive (+) strand. Annealing the primers to denatured nucleic acid followed by extension with an enzyme, such as the large fragment of DNA Polymerase I (Klenow) or Taq DNA polymerase and nucleotides or ligases, results in newly synthesized + and − strands containing the target nucleic acid. Because these newly synthesized nucleic acids are also templates, repeated cycles of denaturing, primer annealing, and extension results in exponential production of the region (i.e., the target mutant nucleotide sequence) defined by the primer. The product of the amplification reaction is a discrete nucleic acid duplex with termini corresponding to the ends of the specific primers employed. Those of skill in the art will know of other amplification methodologies which can also be utilized to increase the copy number of target nucleic acid.

The oligonucleotide primers for use in the invention may be prepared using any suitable method, such as conventional phosphotriester and phosphodiester methods or automated embodiments thereof. In one such automated embodiment, diethylphosphoramidites are used as starting materials and may be synthesized as described by Beaucage, etal. (*Tetrahedron Letters*, 22:1–1862, 1981). One method for synthesizing oligonucleotides on a modified solid support is described in U.S. Pat. No. 4,458,066. One method of amplification which can be used according to this invention is the polymerase chain reaction (PCR) described in U.S. Pat. Nos. 4,683,202 and 4,683,195.

The nucleic acid from any histologic tissue specimen, in purified or nonpurified form, can be utilized as the starting nucleic acid or acids, provided it contains, or is suspected of containing, the specific nucleic acid sequence containing the target nucleic acid. Thus, the process may employ, for example, DNA or RNA, including messenger RNA (mRNA), wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The mutant nucleotide sequence to be amplified may be a fraction of a larger molecule or can be present initially as a discrete molecule, such that the specific sequence constitutes the entire nucleic acid. It is not necessary that the sequence to be amplified be present initially in a pure form; It may be a minor fraction of a complex mixture, such as contained in whole human DNA.

Where the target neoplastic nucleotide sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means; the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP which is known to denature DNA. The reaction conditions suitable for strand separation of nucleic acids with helicases are described by Kuhn Hoffmann-Berling (CSH-*Quantitative Biology*, 43:63, 1978) and techniques for using RecA are reviewed in C. Radding (*Ann. Rev. Genetics*, 16:405–437, 1982).

If the nucleic acid containing the target nucleic acid to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

In some amplification embodiments, the substrates, for example, the deoxyribonucleotide triphosphates dATP, dCTP, dGTP, and dTTP, are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C.

The agent for polymerization may be any compound or system which will function to accomplish the synthesis of primer extension products, including enzymes. Suitable enzymes for this purpose include, for example, *E. coli* DNA polymerase I, Taq polymerase, klenow fragment of *E. coli* DNA polymerase I, T4 DNA polymerase, other available DNA polymerases, polymerase muteins, reverse transcriptase, ligase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each mutant nucleotide strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above. In any event, the method of the invention is not to be limited to the embodiments of amplification which are described herein.

The newly synthesized mutant nucleotide strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleosides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the target mutant nucleotide sequence to the extent necessary for detection. The amount of the mutant nucleotide sequence produced will accumulate in an exponential fashion.

The amplified product may be detected by Southern blot analysis, without using radioactive probes. In such a process, for example, a small sample of DNA containing a very low level of mutant nucleotide sequence is amplified, and analyzed via a Southern blotting technique. The use of non-radioactive probes or labels is facilitated by the high level of the amplified signal.

Nucleic acids having a mutation detected in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988). Thus, in a preferred embodiment where the mutant nucleotide sequence to be detected is a p53 mutation, a hybridization probe is utilized which is capable of hybridizing with mutant nucleotide sequences comprising:

a) 5'-CACAAACATGCACCTCAA-3' ($His^{273}$) (SEQUENCE ID NO. 9);

b) 5'-TCTCCCAGTACAGGCACA-3' ($Thr^{278}$) (SEQUENCE ID NO. 10); or c) 5'-TGCGCCGGCCTCTCCCA-3' ($Gly^{281}$) (SEQUENCE ID NO. 11); and d) sequences complementary to a.) through c.).

In addition, hybridization probes described in Table 1 are utilized to detect the listed mutant p53 sequences. The wild type p53 is generally detected by hybridizing with a nucleotide probe that hybridizes with a nucleotide sequence comprising 5'-CCGGTTCATGGCGCCCAT-3' (SEQUENCE ID NO. 12), although any probes can be utilized that hybridize with any p53 nucleotide sequence that is not subject to mutation.

The invention also provides nucleotide sequence mutations associated with a neoplasm, wherein the mutation is present at p53 codons 180, 187, 193, and 306. These codon orientations are according to Matlashewski G., et al., *Embo Journal*, 3: (13):3257–62, 1984 and Lamb, P., et al., *Molecular & Ceiuluar Biology*, 6(5):1379–85, 1986. The nucleotide sequences of the mutations include: codon 180, GAG to TAG; codon 187, GGT to GAT; codon 193, CAT to CGT; and 306, CGT to TGA. Other mutations at these codons are also included. In accordance with the present invention, these mutations are generally found in head and neck tumors, although they may be present in other neoplastic cells as well.

In an embodiment of the invention, purified nucleic acid fragments containing intervening sequences or oligonucleotide sequences of 10–50 base pairs are radioactively labelled. The labelled preparations are used to probe nucleic acid from a histologic specimen by the Southern hybridization technique. Nucleotide fragments from a histologic specimen, before or after amplification, are separated into fragments of different molecular masses by gel electrophoresis and transferred to filters that bind nucleic acid. After exposure to the labelled probe, which will hybridize to nucleotide fragments containing target nucleic acid sequences, binding of the radioactive probe to target nucleic acid fragments is identified by autoradiography (see *Genetic Engineering*, 1, ed. Robert Williamson, Academic Press, (1981), 72–81). Alternatively, nucleic acid from the specimen can be bound directly to filters to which the radioactive probe selectively attaches by binding nucleic acids having the sequence of interest. Specific sequences and the degree of binding is quantitated by directly counting the radioactive emissions.

Where the target nucleic acid is not amplified, detection using an appropriate hybridization probe may be performed directly on the separated mammalian nucleic acid. In those instances where the target nucleic acid is amplified, detection with the appropriate hybridization probe would be performed after amplification.

The probes of the present invention can be used for examining the distribution of the specific fragments detected, as well as the quantitative (relative) degree of binding of the probe for determining the occurrence of specific strongly binding (hybridizing) sequences, thus indicating the likelihood for an individual to be at low risk or high risk for neoplastic disease, such as head and neck squamous cell carcinoma.

For the most part, the probe will be detectably labelled with an atom or inorganic radical, most commonly using radionuclides, but also heavy metals can be used. Conveniently, a radioactive label may be employed. Radioactive labels include $^{32}P$, $^{125}I$, $^{3}H$, $^{14}C$, $^{111}In$, $^{99m}Tc$, or the like. Any radioactive label may be employed which provides for an adequate signal and has sufficient half-life. Other labels include ligands, which can serve as a specific binding pair member for a labelled ligand, and the like. A wide variety of labels routinely employed in immunoassays can readily be employed in the present assay. The choice of the label will be governed by the effect of the label on the rate of hybridization and binding of the probe to mutant nucleotide sequence. It will be necessary that the label provide sufficient sensitvity to detect the amount of mutant nucleotide sequence available for hybridization.

Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an a $^{32}P$-dNTP or terminal phosphate hydrolysis with alkaline phosphatase followed by labeling with radioactive $^{32}P$ employing $^{32}P$-NTP and T4 polynucleotide kinase. Alternatively, nucleotides can be synthesized where one or more of the elements present are replaced with a radioactive isotope, e.g., hydrogen with tritium. If desired, complementary labelled strands can be used as probes to enhance the concentration of hybridized label.

Where other radionucleotide labels are involved, various linking groups can be employed. A terminal hydroxyl can be esterified, with inorganic acids, e.g., $^{32}P$ phosphate, or $^{14}C$ organic acids, or else esterified to provide linking groups to the label. Alternatively, intermediate bases may be substituted with activatable linking groups that can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2,3-dihydrophthalazinediones (e.g., luminol).

The probe can be employed for hybridizing to a nucleotide sequence affixed to a water insoluble porous support. Depending upon the source of the nucleic acid, the manner in which the nucleic acid is affixed to the support may vary. Those of ordinary skill in the art know, or can easily ascertain, different supports that can be used in the method of the invention.

The nucleic acid from a histologic specimen is cloned and then spotted or spread onto a filter to provide a plurality of individual portions (plaques). The filter is an inert porous solid support, e.g., nitrocellulose. Any cells (or phage) present in the specimen are treated to liberate their nucleic acid. The lysing and denaturation of nucleic acid, as well as the subsequent washings, can be achieved with an appropriate solution for a sufficient time to lyse the cells and denature the nucleic acid. For lysing, chemical lysing will conveniently be employed, as described previously for the lysis buffer. Other denaturation agents include elevated temperatures, organic reagents, e.g., alcohols, amides, amines, ureas, phenols and sulfoxides or certain inorganic ions, e.g., thiocyanate and perchlorate.

After denaturation, the filter is washed in an aqueous buffered solution, such as Tris, generally at a pH of about 6 to 8, usually 7. One or more washings may be involved, conveniently using the same procedure as employed for the lysing and denaturation. After the lysing, denaturing, and washes have been accomplished, the nucleic acid spotted filter is dried at an elevated temperature, generally from about 50° C. to 70° C. Under this procedure, the nucleic acid is fixed in position and can be assayed with the probe when convenient.

Pre-hybridization may be accomplished by incubating the filter with the hybridization solution without the probe at a mildly elevated temperature for a sufficient time to thoroughly wet the filter. Various hybridization solutions may be employed, comprising from about 20% to 60% volume, preferably 30%, of an inert polar organic solvent. A common hybridization solution employs about 50% formamide, about 0.5 to 1M sodium chloride, about 0.05 to 0.1M sodium citrate, about 0.05 to 0.2% sodium dodecylsulfate, and minor amounts of EDTA, ficoll (about 300–500 kD), polyvinylpyrrolidone, (about 250–500 kD) and serum albumin. Also included in the hybridization solution will generally be from about 0.5 to 5 mg/ml of sonicated denatured DNA, e.g., calf thymus of salmon sperm; and optionally from about 0.5 to 2% wt/vol glycine. Other additives may also be included, such as dextran sulfate of from about 100 to 1,000 kD and in an amount of from about 8 to 15 weight percent of the hybridization solution.

The particular hybridization technique is not essential to the invention. Other hybridization techniques are described by Gall and Pardue, (*Proc. Natl. Acad. Sci.* 63:378, 1969); and John, et al., (*Nature*, 223:582, 1969). As improvements are made in hybridization techniques they can readily be applied in the method of the invention.

The amount of labelled probe present in the hybridization solution will vary widely, depending upon the nature of the label, the amount of the labelled probe that can reasonably bind to the filter, and the stringency of the hybridization. Generally, substantial excess over stoichiometric concentrations of the probe will be employed to enhance the rate of binding of the probe to the fixed target nucleic acid.

Various degrees of stringency of hybridization may be employed. The more severe the conditions, the greater the complementarily that is required for hybridization between the probe and the single stranded target nucleic acid sequence for duplex formation. Severity can be controlled by temperature, probe concentration, probe length, ionic strength, time, and the like. Conveniently, the stringency of hybridization is varied by changing the polarity of the reactant solution by manipulating the concentration of formamide in the range of 20% to 50%. Temperatures employed will normally be in the range of about 20° C. to 80° C., usually 30° C. to 75° C. (see, generally, *Current Protocols in Molecular Biology*, Ausubel, ed., Wiley & Sons, 1989).

After the filter has been contacted with a hybridization solution at a moderate temperature for a period of time sufficient to allow hybridization to occur, the filter is then introduced into a second solution having analogous concentrations of sodium chloride, sodium citrate and sodium dodecylsulfate as provided in the hybridization solution. The time the filter is maintained in the second solution may vary from five minutes to three hours or more. The second solution determines the stringency, dissolving cross duplexes and short complementary sequences. After rinsing the filter at room temperature with dilute sodium citrate-sodium chloride solution, the filter may now be assayed for the presence of duplexes in accordance with the nature of the label. Where the label is radioactive, the filter is dried and exposed to X-ray film.

The label may also comprise a fluorescent moiety that can then be probed with a specific antifluorescent antibody. For example, horseradish peroxidase enzyme can be conjugated to this antibody to catalyze a chemiluminescent reaction. Production of light can then be seen on rapid exposure to film.

The present invention identifies mutations in a target sequence, such as p53, that are unique to the primary tumor isolated from a subject and metastatic sites derived from the primary tumor. In the tumor cells, the mutated nucleotide sequence is expressed in an altered manner as compared to expression in a normal cell; therefore, it is possible to design appropriate therapeutic or diagnostic techniques directed to this specific sequence. Thus, where a cell-proliferative disorder is associated with the expression of a particular mutated proto-oncogene or tumor suppressor gene nucleic acid sequence, a nucleotide sequence that interferes with the specific expression of the mutated gene at the transcriptional or translational level can be used. This approach utilizes, for example, antisense oligonucleotides and/or ribozymes to block transcription or translation of a specific mutated mRNA, either by masking that mRNA with an antisense nucleic acid or by cleaving it with a ribozyme.

Antisense nucleic acids are DNA or RNA molecules that are complementary to at least a portion of a specific mRNA molecule (Weintraub, *Scientific American*, 262:40, 1990). To date, several tumor suppressor genes and oncogenes have been targeted for suppression or down-regulation including, but not limited to, p53 (V. S. Prasolov et al., *MoL Biol.* (Moscow) M:22:1105–1112, 1988); ras (S. K Anderson et al., Mol *Immunol*. 26:985–991, 1989; D. Brown et al., Oncogene Res. 4:243–249, 1989); fos (B. Levi et al., Cell. Differ. Dev. 25 (Suppl):95–102, 1988; D. Mercola et al., Gene 72:253–265, 1988); and myc (S. O. Freytag, Mol. Cell. Biol. 8:1614–1624, 1988; E. V. Prochownik et al., Mol Cell. Biol 8:3683–3695, 1988; S. L. Loke et al., Curr. Top. Microbiol Immunol. 141:282–288, 1988).

It is not sufficient in all cases to block production of the target mutant gene. As described in A. J. Levine, et al., (Biochimica et Biophisica Acta., 1032:119–136, 1990), there are at least five types of mutations that can contribute to the tumor phenotype. Briefly, Type I mutations are those mutations in genes that result in abnormal protein products, which act in a positive dominant fashion. Examples of such mutations are those in H-ras and K-ras genes that result in amino acid changes at positions 12 or 61 in the protein, leading to a protein that binds GTP and is constantly signaling for cell growth. Type II mutations are those that result in overproduction of an oncoprotein, such as the berabl translocation that results in overproduction of a normal myc protein and an altered abi protein. Type III mutations are loss of function mutations wherein tumors arise as the result of loss of both alleles, such as with the retinoblastoma sensitivity gene (Rb) on human chromosome 13q14 and the Wilm's tumor sensitivity gene localized at 11q13. In 75% of colorectal carcinomas, one allele at the p12-p13.3 locus of chromosome 17 containing the p53 gene is commonly deleted, and in some cases the other p53 allele which remains in the colorectal cancer cells has been shown to produce a mutant p53 protein that presumably contributes to tumorigenesis. Type IV mutations are those that result in expression of a protein that does not directly contribute to the growth of cells, but enhances the ability of cancer cells to survive. For instance, mutations to the v-erb-A gene results in erythoblasts transformed with the altered gene being kept in the replication cycle. Type V mutations result from addition of new genetic information into tumor cells, commonly by way of a virus. In some cases the virus integrates its DNA into the cellular genome to produce proteins that bind to cellular negative regulators of growth, such as RB and p53, and thus, in effect, mimic the Type III loss of function mutation mechanism.

Antisense therapy can be used to block production of mutant proteins that act directly to increase the probability of producing neoplastic cells, such as in mechanism Type III, Type IV and Type V mutations that mimic Type III. Antisense is also therapeutically effective when mutation is not dominant, for instance when a non-mutant allele remains that encodes the proper protein. However, when the mutation is dominant, as in Type I mutations, and in cases wherein either both alleles are deleted or one is deleted and the other is mutant, as in certain Type III mutations, antisense therapy is preferably accompanied by replacement therapy. In replacement therapy a wild type gene is introduced into the target cells identified as having a mutant tumor suppressor gene or protooncogene which results in production of the wild type protein necessary to forestall development of the neoplasia associated with the identified mutant gene(s).

In the case of tumor suppressor genes, it is known that introducing a suppressor gene into cultured cells either causes cell death or causes no discernible changes, however, the cells may no longer be tumorigenic in animals. Thus, in cases where ribozyme and/or antisense therapy is accompanied by gene replacement therapy, the chances are increased that the cell population containing the mutant gene for which the ribozyme or antisense oligonucleotide is specific will no longer contribute to development of neoplasia in the subject being treated.

Synthetic antisense oligonucleotides are generally between 15 and 25 bases in length. Assuming random organization of the human genome, statistics suggest that a 17-mer defines a unique sequence in the cellular mRNA in human DNA; a 15-mer defines a unique sequence in the cellular mRNA component. Thus, substantial specificity for a selected genetic target is easily obtained using the synthetic oligomers of this invention.

In the cell, the antisense nucleic acids hybridize to the corresponding mRNA, forming a double-stranded molecule. The antisense nucleic acids, interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target nucleotide mutant producing cell. The use of antisense methods to inhibit the in vitro translation of genes is well known in the art (Marcus-Sakura, Anal.Biochem., 172:289, 1988). Less commonly, antisense molecules which bind directly to the DNA may be used.

Ribozymes are RNA molecules possessing the ability to specifically cleave other single-stranded RNA in a manner analogous to DNA restriction endonucleases. Through the modification of nucleotide sequences that encode these RNAs, it is possible to engineer molecules that recognize specific nucleotide sequences associated with production of a mutated proto oncogene or tumor suppressor gene in an RNA molecule and cleave it (Cech, J.Amer.Med. Assn., 260:3030, 1988). A major advantage of this approach is that, because they are sequence-specific, only target mRNAs with particular mutant sequences are inactivated.

There are two basic types of ribozymes, namely, tetrahymena-type (Hasselhoff, Nature, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species, and 18-based recognition sequences are preferable to shorter recognition sequences.

Unmodified oligodeoxyribonucleotides are readily degraded by serum and cellular nucleases. Therefore, as is well known in the art, certain modifications of the phosphate backbone have conferred nuclease resistance to antisense DNA. For instance phosphorothioate, methylphosphonate, and α-anomeric sugar-phosphate, backbone-modified oligomers have increased resistance to serum and cellular nucleases. In addition, methylphosphonates are nonionic and offer increased lipophilicity to improve uptake through cellular membranes. The use of modified oligonucleotides as antisense agents may require slightly longer or shorter sequences because chemical changes in molecular structure can affect hybridization (L. A. Chrisey et al., BioPharm 4:36–42, 1991). These backbone-modified oligos bind to a target sequence and exert their inhibitory effects by blocking the binding of the cell's translational machinery to a specific RNA or by inducing ribonuclease H activity through the formation of RNA/DNA duplex structures.

The present invention also provides gene therapy for the treatment of cell proliferative or immunologic disorders that are mediated by a mutated proto-oncogene or tumor suppressor gene, such as a mutated p53 gene sequence. Such therapy would achieve its effect by introduction of the specific antisense polynucleotide and/or replacement wild type gene into cells identified by the methods of this invention as having the proliferative disorder caused by mutated genes. Whether the cell will require replacement of the wild type gene encoding the tumor suppressor gene or proto-oncogene as well as antisense therapy to prevent replication of the mutant gene must be determined on a case by case basis and will depend upon whether the mutation has a dominant effect, ie., whether both alleles of the wild type gene have been destroyed so that total absence of the gene has a cell proliferative effect.

Delivery of antisense proto-oncogene or tumor suppressor polynucleotides specific for mutated genes as well as of replacement wild type genes can be achieved using a recombinant expression vector such as a chimeric virus or a colloidal dispersion system. Preferred for therapeutic delivery of antisense sequences is the use of liposomes, especially targeted liposomes.

Various viral vectors that can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting one or more sequences of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the proto oncogene or tumor suppressor antisense polynucleotide (i.e., a p 53 antisense polynucleotide). A separate vector can be utilized for targeted delivery of a replacement gene to the cell(s), if needed, or the antisense oligonucleotide and the replacement gene can optionally be delivered via the same vector since the antisense oligonucleotide is specific only for the mutant target gene.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include, but are not limited to, Ψ2, PA317 and PA12, for example. These cell lines produce empty virions, since no genome is packaged. If a retroviral vector is introduced into such helper cells in which the packaging signal is intact, but the structural genes are replaced by other genes of interest, the vector can be packaged and vector virion can be produced.

Another targeted delivery system for antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem*. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method.

For example, one of the container means may comprise a hybridization probe that is or can be detectably labelled. A second container may comprise a cell lysis buffer. The kit may also have containers holding nucleotide(s) for amplification of the target nucleic acid sequence and/or a container comprising a reporter-means, such as a biotin-binding protein, such as avidin or streptavidin, bound to a reporter molecule, such as an enzymatic, fluorescent, or radionuclide label.

The above disclosure generally describes the present invention. A more complete understanding can be obtained by reference to the following specific examples which are provided herein for purposes of illustration only and are not intended to limit the scope of the invention.

EXAMPLES

The histopathologic surgical margins, lymph nodes and oral cavity swabs from at least twenty patients were assessed for p53 mutations. Molecular analysis identified clonal tumor cells in approximately 50% of the margins and 25% of the lymph nodes from head and neck cancer patients initially believed to be negative by light microscopy.

The results show that approximately 45% of invasive head and neck squamous cell carcinoma (HNSCC) tumors have a mutated p53 gene as determined by sequencing of primary tumor DNA.

Example 1
A. PROCESSING OF HISTOPATHOLOGIC TISSUE

1. Surgical Margins

Following incision of a primary tumor, a defect is left in the area where the tumor has been removed. Surgical margins have been determined by frozen section and/or embedded in paraffin for final assessment by light microscopy. In the defect that is left, a small representative section of tissue (approximately 1 mm×0.5 mm) was taken from all four quadrants of each sample and was placed in separate 1.8 ml cryostat tubes. The samples were immediately frozen and analyzed.

2. Lymph Node Analysis

Following standard visualization of representative sections by light microscopy, each of the remaining lymph nodes were placed in separate 1.8 mm cryostat tubes. The samples were immediately frozen and analyzed.

A representative section was taken from each surgical margin and lymph node, stained by standard H & E staining, and visualized under light microscopy. One-hundred 12μ sections were then cut and placed into 1% SDS and 5 mg/ml of proteinase K. A final section was take, stained by standard H & E, and also visualized by light microscopy. The DNA was digested at 60° C. for 4 hours. The DNA was extracted twice with phenol and chloroform by standard methods and then precipitated with ethanol. The DNA was washed with 70% ethanol, dried, and resuspended in 50 ml of Tris-EDTA. The target p53 fragment was then amplified from each of the surgical margins and lymph nodes as described below.

B. PCR AMPLIFICATION OF TARGET GENE (p53)

1. For p53 (exons 5–9), amplify 1800 bp DNA fragment:

| | |
|---|---|
| Margin or lymph node DNA | 5 ul |
| Distilled water | 34 ul |
| PCR buffer(10 X) | 5 ul |
| dNTP | 3 ul |
| Primer 4S | 1 ul |
| Primer 9AS | 1 ul |
| Taq(polymerase, 5 U/ul) | 1 ul |

4S 5'-GTA GGA ATT CAC TTG TGC CCT GAC TTG-3' (SEQ. ID. NO. 13)

9AS 5'-CAT CGA ATT CTG GM ACT TTC CAC TTG AT-3' (SEQ ID NO. 14)

The sample was placed in a 500 ul tube to which 2 drops of mineral oil were added. The sample was amplified in an Omnigene PCR machine, as follows: 950° C. for 30 sec.; 60° C. for 1 min. 35 cycles; 70° C. for 1 min.; and 70° C. for 5 min. 1 cycle.

All amplifications were performed with negative control (water devoid of any DNA) and positive (cell line DNA) controls, such as SW480 (12 vat mutation, K-ras) or DZ74 (273 cys mutation, p53).

C. CLONING

To 5 ul of the PCR product above, 5 ul of 2× stop buffer (Bromophenol blue in Ficoll, glycerol and sarcosyl with tris-acetate buffer) was added. The samples were run on 1% or 2% agarose gels to observe the yield of amplification. The remaining 45 ul of the PCR product, was mixed with 155 ul distilled water. To the 200 ul PCR mixture, 200 ul PC-9 (Gibco-BRL), was added and vortexed well. The tube was spun for 2 minutes in Hermle Z230 M (Hermle, Germany) table centrifuge at high speed. The supernatant was removed to another tube and the pellet was treated with PC-9 one more time.

The supernatant was removed to a new 1.5 ml tube and 66 ul 10 M ammonia acetate, 2 ul glycogen and 660 ul 200 proof ethanol were added and the tube was vortexed well. The tube was spun for 20 min. in a Hermle Z230 M table centrifuge at high speed. The supernatant was decanted and 660 ul 70% ethanol, was added and the solution mixed. The tube was spun for 2 more minutes and decanted again. The sample was dried in a HETOVAC (Heto, Denmark).

An alternative method for enrichment of malignant epithelial cells and elimination of non-epithelial cells in the tissue sample, prior to PCR, is as follows. Lymph node cells were isolated by enzymatic digestion in 0.1 g DNAse (SIGMA) and 1 g collagenase Type VIII (SIGMA) in 10 mm Hepes for 15–30 minutes at 37° C. Cells were washed twice in HBSS with 2% fetal calf serum (FCS) and resuspended in 1 ml. The cell suspension was cooled on ice and 20 ug/ml of a monoclonal antibody with specificity for epithelial cells, EBA-1 (other antibodies with specificity for epithelial cells would be equally effective) was added to the cell suspension and incubated on ice for one hour. The cells were washed twice in cold (2–8° C.) HBSS with 2% FCS. The cells were resuspended in cold HBSS/2% FCS at a cell concentration of 2–4×10$^6$ per ml.

Primary EBA antibodies bound to epithelial cells were isolated on magnetic, Dynabeads (Dynal International, Oslo, Norway) as follows. Dynabeads M-450 were coated with a secondary antibody (sheep-antimouse, by the manufacturer). The beads were first washed twice for 5 minutes at 2–8° C. in phosphate buffered saline (PBS), pH 7.4, containing 0.1% FCS. The Dynabeads were collected using a magnet and the supernatant was discarded and the beads resuspended in equivalent initial volume.

The Dynabeads coated with the secondary anti-murine antibody at a ratio of 5 particles per target cell were added to the lymph node sample. The concentration should be about 10$^7$ beads per ml of solution. The mixture was incubated for 30 minutes at 4° C. on a Rock-N-Roller. Cold (4–8° C.) HBSS with 1% FCS was added in a volume at least 4× the volume of the bead/cell suspension. The Dynabeads were concentrated using the magnet. The supernatant was removed and the beads washed thoroughly 3 times using HBSS/1% FCS in a volume equal to that above (at least 4× the volume of the bead/cell suspension). The Dynabead/cell suspension was centrifuged at 1,000×g and resuspended in SDS/Proteinase K and DNA isolated for PCR.

DNA was resuspended by adding 4 to 8 ul of distilled water depending on the size of the pellet. Two ul of DNA was mixed with 1 ul T4 Lambda Zap II (Stratagene, La Jolla, Calif.) 1 ul T4 ligation buffer (5×). The DNA mixture was incubated at 65° C. for 5 min., 37° C. for 5 min. and 24° C. for 5 min. in a water bath. One ul of T4 ligase was added and the mixture was incubated at 15° C. for 4 to 6 hours. One ul of the ligated product was mixed with 2.4 ul packaging extract (Stratagene) (Red) and 3.75 ul packaging extract (Yellow). The ligation mixture was kept at room temperature for 2 hours. 250 ul phage dilution buffer (stock phage) was added to the mixture after 2 hours.

About 10 ul to 100 ul stock phage were added to 100 ul XL1-B cells and incubated at 37° C. for 10 min. 4 ml of 55° C. top agarose was added and the mixture was plated on L-Agar gel plates at 37° C. overnight.

D. HYBRIDIZATION

A piece of nylon hybridization transfer membrane (Zetaprobe, BioRad, Richmond, Calif.) was laid on the surface of the gel which contains lysis plaques for 1 min. The membrane was then transferred to on a blot paper soaking 0.5 M NaOH, plaque side up for 15 min. The membrane was then rinsed in 2×SSC for 5 min. twice. The membrane was then placed on a blot paper before crosslinking under UV light for 30 seconds. The membranes were then placed in plastic bags for hybridization.

Oligomers (Table 2) were radioactively labeled using $^{32}$P γ-ATP by standard methods (T4 kinase). Sixty ng of the oligomer (melting temperature varied from 52° C. to 60° C.-see Table 2) was dissolved in 6 ul distilled water. 1 ul of 10×kinase buffer and 2 ul of $\gamma^{32}$-P-ATP were added to the oligo and incubated at 65° C. for 5 minutes. After 5 minutes the tube was spun down and 1 ul of T4 kinase was added and incubated at 37° C. for 30 minutes. The kinased product was isolated by standard spin column protocols.

The labelled probes were added to bags containing plaque lifts. Hybridization was performed at the temperature which is 10° C. below the melting temperature of the probe for 1 hour in a shaking bath. The membranes were then removed and washed in 3×SSC/0.1% SDS at room temperature for 5 min. and in 3×SSC/0.1% SDS at the melting temperature of the probe for 30 min. The excess solution was removed from the membrane before wrapping in Saran Wrap. The membranes were exposed at −80° C. for 4 hours or overnight.

TABLE 2

Oligomers Used In Head and Neck p53 Detection

| SEQUENCE ID NO. | CODON | | MT |
|---|---|---|---|
| 15. 5'-CCTGCAGTAGTCCCCTG-3' | (codon 126 TAC to TAG) | | MT. 56° C. |
| 16. 5'-CCTCAACAGGATGTTTTG-3' | (codon 126 TAC to TA) | | MT. 52° C. |
| 17. 5'-GCAGCTGTGAGTTGATTC-3' | (codon 146 TGG to TGA) | | MT. 54° C. |
| 18. 5'-GCCCGGCCCCCGCGTC-3' | (codon 155 ACC to CCC) | | MT. 62° C. |
| 19. 5'-CCGCGTCTGCGCCATG-3' | (codon 158 CGC to TGC) | | MT. 56° C. |
| 20. 5'-GGCCATCCACAAGCAGT-3' | (codon 163 TAC to CAC) | | MT. 54° C. |
| 21. 5'-ACAGCACACGACGGAGG-3' | (codon 169 ATG to ACG) | | MT. 56° C. |
| 22. 5'-CGGAGGTTCTGAGGCGC-3' | (codon 173 GTG to CTG) | | MT. 56° C. |
| 23. 5'-TTGTGAGGCACTGCCCC-3' | (codon 175 CGC to CAC) | | MT. 56° C. |
| 24. 5'-AGGCGCTTCCCCCACC-3' | (codon 176 TGC to TTC) | | MT. 56° C. |
| 25. 5'-CCCCACCGTGAGCGCT-3' | (codon 179 CAT to CGT) | | MT. 56° C. |
| 26. 5'-ATCCGAGTGAAAGGAAATT-3' | (codon 198 GAA to AAA) | | MT. 52° C. |
| 27. 5'-TGTGGAGTCTTTGGATGA-3' | (codon 205 TAT to TCT) | | MT. 52° C. |
| 28. 5'-TGTGGAGGATTTGGATGA-3' | (codon 205 TAT to GAT) | | MT. 52° C. |
| 29. 5'-TGTGGAGTGTTTGGATGA-3' | (codon 205 TAT to TGT) | | MT. 52° C. |
| 30. 5'-ACACTTTTTGACATAGTGT-3' | (codon 213 CGA to TGA) | | MT. 50° C. |
| 31. 5-CCCCACCTTGAGCGCT-3' | (codon 179 CAT to CTT) | | MT. 54° C. |
| 32. 5'-ACATAGTATGGTGGTGCC-3' | (codon 216 GTG to ATG) | | MT. 54° C. |
| 33. 5'-ACATAGTTTTGTGGTGCC-3' | (codon 216 GTG to TTT) | | MT. 52° C. |
| 34. 5'-GGTGCCCTGTGAGCCG-3' | (codon 220 TAT to TGT) | | MT. 56° C. |
| 35. 5'-GGTGCCCCATGAGCCG-3' | (codon 220 TAT to CAT) | | MT. 56° C. |
| 36. 5'-GGTGCCCTCTGAGCCG-3' | (codon 220 TAT to TCT) | | MT. 56° C. |
| 37. 5'-TGGCTCTGAGTGTACCAC-3' | (codon 228 GAC to GAG) | | MT. 56° C. |
| 38. 5'-CATCCACTGCAACTACAT-3' | (codon 234 TAC to TGC) | | MT. 52° C. |
| 39. 5'-CTACAACTAAATGTGTAACA-3' | (codon 236 TAC to TAA) | | MT. 52° C. |
| 40. 5'-CAACTACATTTGTAACAGTT-3' | (codon 237 ATG to ATT) | | MT. 52° C. |
| 41. 5'-CAACTACATATGTAACAGTT-3' | (codon 237 ATG to ATA) | | MT. 52° C. |
| 42. 5'-ACTACATGTTTAACAGTTCC-3' | (codon 238 TGT to TTT) | | MT. 54° C. |
| 43. 5'-ACTACATGTATAACAGTTCC-3' | (codon 238 TGT to TAT) | | MT. 54° C. |
| 44. 5'-CAGTTCCTTCATGGGCG-3' | (codon 242 TGC to TTC) | | MT. 54° C. |
| 45. 5'-GCATGGGCGTTATGAAC-3' | (codon 245 GGC to GTT) | | MT. 52° C. |
| 46. 5'-GCATGGGCTGCATGAAC-3' | (codon 245 GGC to TGC) | | MT. 54° C. |
| 47. 5'-GCATGGGCGACATGAAC-3' | (codon 245 GGC to GAC) | | MT. 54° C. |
| 48. 5'-GGCGGCTTGAACCGGAG-3' | (codon 246 ATG to TTG) | | MT. 58° C. |
| 49. 5'-CATGAACCTGAGGCCCAT-3' | (codon 248 CGG to CTG) | | MT. 56° C. |
| 50. 5'-GCATGAACTGGAGGCCCA-3' | (codon 248 CGG to TGG) | | MT. 58° C. |
| 51. 5'-GCATGAACCAGAGGCCCA-3' | (codon 248 CGG to CAG) | | MT. 58° C. |
| 52. 5'-AACCGGAGTCCCATCCTC-3' | (codon 249 AGG to AGT) | | MT. 58° C. |
| 53. 5'-GAACCGGGGGCCCATC-3' | (codon 249 AGG to GGG) | | MT. 56° C. |
| 54. 5'-GAGGCCCAACCTCACCA-3' | (codon 251 ATC to AAC) | | MT. 56° C. |
| 55. 5'-CATCACACCGGAAGACT-3' | (codon 257 CTG to CCG) | | MT. 52° C. |

TABLE 2-continued

Oligomers Used In Head and Neck p53 Detection

| SEQUENCE ID NO. | CODON | | MT |
|---|---|---|---|
| 56. 5'-TCTACTGGAACGGAACAG-3' | (codon 266 GGA to GAA) | MT. 54° C. |
| 57. 5'-TTGAGGTGCATGTTTGTG-3' | (codon 273 CGT to CAT) | MT. 52° C. |
| 58. 5'-TTGAGGTGGGTGTTTGTG-3' | (codon 273 CGT to GGT) | MT. 54° C. |
| 59. 5'-GCTGTTTATGCCTGCCT-3' | (codon 275 TGT to TAT) | MT. 56° C. |
| 60. 5'-TGCCTGTACTGGGAGAGA-3' | (codon 278 CCT to CTT) | MT. 56° C. |
| 61. 5'-TGCCTGTTCTGGGAGAGA-3' | (codon 278 CCT to TCT) | MT. 56° C. |
| 62. 5'-TGCCTGTCGTGGGAGAGA-3' | (codon 278 CCT to CGT) | MT. 58° C. |
| 63. 5'-CTGTCCTGAGAGAGACC-3' | (codon 279 GGG to GAG) | MT. 54° C. |
| 64. 5'-CTGTCCTGGGGAGAGAC-3' | (codon 279 insert G) | MT. 56° C. |
| 65. 5'-TGGGAGACACCGGCGCA-3' | (codon 281 GAC to CAC) | MT. 58° C. |
| 66. 5'-TGGGAGAGAGCGGCGCA-3' | (codon 281 GAC to GAG) | MT. 58° C. |
| 67. 5'-GCGCACAAAGGAAGAGAA-3' | (codon 285 GA to AAG) | MT. 54° C. |
| 68. 5'-GCACAGAGAAAGAGAATCT-3' | (codon 286 GAA to AAA) | MT. 54° C. |
| 69. 5'-GAAAGGGTAGCCTCACC-3' | (codon 294 GA to TAG) | MT. 54° C. |
| 70. 5'-GAGCCTCCCCACGAGCT-3' | (codon 296 CAC to CCC) | MT. 58° C. |
| 71. 5'-CTCACCACTAGCTGCCC-3' | (codon 298 GA to TAG) | MT. 56° C. |
| 72. 5'-CTCACCACGCACTGCCC-3' | (codon 298 GA to GCA) | MT. 58° C. |
| 73. 5'-GGTGCGTATTTGTGCCT-3' | (codon 274 GTT to ATT | MT. 52° C. |

MT = Melting temperature

Alternatively, the oligomers were labeled using chemiluminescence. 100 pmoles of oligomers was added to 16 ul cacodylate buffer, 10 ul fluorescein-dUDP, 16 ul terminal transferase and water to total 160 ul. The mixture was incubated for 1 hour at 37° C.

Membranes were pre-hybridized for 1 hour in [5×SSC/ 0.02% SDS; 0.5% (w/v) blocking agent (Milk) (Amersham, UK)] The probe was added and hybridization was allowed to go for 1 hour at the temperature which is 10° C. below the melting temperature of the probe in shaking bath. The membranes were washed in 3×SSC/0.1% SDS at room temperature 5 min. twice. The membranes were then washed in 3×SSC/0.1% SDS at the melting temperature of the probe for 15 min. three times in the washing bath. The membranes were then rinsed in TBS for 1 minute followed by incubation in block buffer (5% dry nonfat milk/TBS) for 30 min. The membranes were then rinsed in TBS for 1 min. and incubated in antibody solution (1:5000 anti-fluorescein alkaline phosphatase antibody (Boehringer Mannheim, Indianapolis, Ind.) in 5% milkF/TBS) for 30 minutes. The membrane was then washed in TBS for 5 min. eight times with shaking. The detection reagent lumigen PPD (Boehringer Mannheim, 1:100 in MgCl$_2$, 50 mmol/lit TBS, pH 9.5) were mixed, and the blots incubated in the solution for 1 min. The extra solution was removed and the membrane wrapped with plastic and exposed to X-ray film immediately for 10 to 60 minutes.

E. SINGLE STRANDED HYBRIDIZATION

Prior to the PCR reaction of the target p53 gene, either primer must be phosphorylated at the 5' site. Half of the PCR reaction was digested with lamda exonuclease allowing only digestion of phosphorylated strand. The product was then run on a spin column and DNA free of primers and enzyme was isolated. Single stranded DNA was run on an agarose gel and transferred by standard techniques. Oligomer specific hybridization with either radiolabeted or chemiluminescence labeled probes was performed as described below. A positive signal was detected by exposure to X-ray film.

Example 2

The case for presentation was selected from a group of individuals with HNSCC enrolled in a research protocol to investigate p53 gene mutations in this disease. The protocol was approved by The Johns Hopkins University Joint Committee on Clinical Investigation. The patient had provided written informed consent for participation in the study.

PM is a 58-year-old woman who presented to her dentist with a history of sores in her mouth for several months. She had been a smoker of one pack per day and had regularly used alcohol in the past. Physical examination revealed a fungating mass in the left retromolar trigone (RMT) which measured 5×3 cm. A separate, 3×2.5 cm ulcerative mass was noted on the right posterior maxillary alveolar ridge (ALV). On the anterior floor of mouth (FOM) a 5 mm patch of leukoplakia was present (FIG. 1). Biopsy of the lesions showed that the two larger ones were both infiltrating moderately differentiated squamous cell carcinoma (SCC) while the FOM lesion consisted of severe dysplasia. There was a single palpable mobile node in the left midjugular region and a second in the right upper jugular chain, both approximately 2-cm in diameter. A CT scan showed bony erosion of the right maxillary alveolus but no invasion of the left mandible. Panendoscopy revealed no other lesions of the upper aerodigestive tract.

One month after diagnosis, the patient underwent resection of both invasive cancers via midline mandibulotomy with bilateral neck dissections. The right palate was repaired using a temporalis muscle flap and the left RMT was reconstructed using a pectoralis major myocutaneous flap. Standard pathologic evaluation of the specimens revealed all mucosal margins to be free of tumor, both on frozen and permanent section. Deep soft tissue margins from both the ALV and RMT resections were read as focally positive for tumor. The right neck had one level I and one level III lymph node with metastatic squamous carcinoma. Forty-six other lymph nodes were negative for tumor. The left neck had a single level 11 node with metastatic squamous carcinoma and 35 nodes with no tumor.

At surgery, samples of the three oral lesions together with resection margins from each of the two infiltrating carcinomas were sent for molecular analysis of the p53 genes. In addition, formalin-fixed tissue from the lymph nodes were submitted for analysis.

The patient went on to receive 6,600 rads external beam radiation therapy. Six months later an ulcer developed on the right palate posterior to the site of the resected right ALV lesion which was biopsied and again showed SCC. A swab of the oral cavity with gloved finger and tongue blade was obtained. The persistent tumor was then removed by wide local excision. Once again all deep and mucosal margins were negative for tumor on frozen section. Adjacent marginal tissue was again sent for p53 mutation screening. The palate defect was filled with a dental obturator. The patient remains disease free two months after salvage surgery.

Samples from the two invasive carcinomas and the FOM dysplastic lesion as well as the recurrent right ALV tumor were rapidly frozen in OCT (Tissue Tek, Elkhart, Ind.), a polyglycol embedding medium. Cryostat sections were examined with hematoxylin and eosin stain to ensure that the tissue consisted of at least 50% tumor cells. Over fifty 12-micron sections were then cut and placed in SDS/proteinase K to dissolve proteins. DNA was extracted with phenol/chloroform and precipitated with ethanol. A 1.8 kilobase segment of the p53 gene including exons 5 to 9 was amplified by PCR as described in Example 1 (Sidransky, D., et al., *Science*, 2:706–709, 1991). The UDP cloning site was added to the 5' end of the primers to permit cloning into a clone amp (BRL) plasmid vector (pSPORT) (See Example 3) (J. O. Boyle et al., *Cancer Research*, In press). Following amplification with uracil-containing primers, PCR products were extracted with phenol/chloroform, gel purified, and treated with UDP, and one half of the total product was annealed to the plasmid vector according to the manufacturer's instructions (Buchman, G W, et al., *Focus*, 14:41–45, 1992). Competent DH5-alpha cells were transfected with plasmid by heat shock, plated onto ampicillin plates, and incubated overnight at 37° C. Over 100 colonies were pooled and DNA was isolated from plasmid by alkaline lysis and precipitation in isopropanol.

Double-stranded DNA from plasmid was sequenced by the dideoxy method as described in Sidransky, D., et al., supra. Sequencing reaction products were separated on a 6% ureal polyacrylamide gel and exposed to film. All mutations were confirmed by repeating the PCR reaction followed by recloning and resequencing.

Detection of Mutation DNA Sequences in Other Clinical Specimens

When specific p53 point mutations had been identified and confirmed in the fresh tumor specimens, mutant-specific oligomer probes were synthesized for each tumor. Probe sequences were:

codon 278: 5'-TGTGCCTGTACTGGGAGA-3' (RMT) (SEQ ID NO. 74)

codon 281: 5'-TGGGAGACACCGGCGC-3' (ALV) (SEQ ID NO. 75)

DNA was extracted from fresh tumor margins, exfoliated cells from oral swabs, and cervical nodal tissue as described in Sidransky, D., et al., supra. A portion of the p53 gene (exons 7 and 8) was amplified by PCR from each sample and cloned into a Lambda Zap phage vector (Stratagene). Phage were plated and plaques were immobilized onto nylon filters, then probed with the two $^{32}$P labeled DNA probes specific for each missense mutation as described in Sidransky, D., et al., supra., and in Sidransky, D., et al., (*Science*, 256:102–105, 1992)

Figure 2:
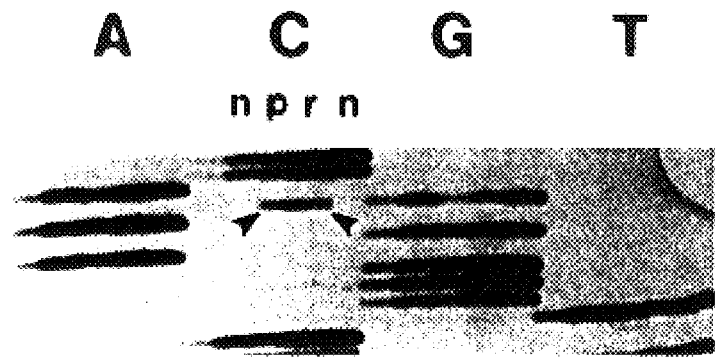
FIG. 2 is an autoradiograph of sequencing gel demonstrating p53 mutation in DNA from ALV tumor samples. (n)=normal DNA from peripheral blood lymphocytes; (p)= primary ALV tumor; (r)=recurrent tumor. p and r contain the identical G→C transversion (arrows) in codon 281. A,C,G,T indicate adenosine, cytosine, guanine and thymidine.

A different missense point mutation was identified in the p53 gene in each of the two invasive carcinomas. FIG. 2 shows an autoradiograph of a sequence gel showing p53 mutations in DNA from ALV tumor samples. (n)=normal DNA from peripheral blood lymphocytes; (p)=primary ALV tumor; (r)=recurrent tumor, p and r contain the identical G→C transversion (arrows) in codon 281. The left RMT trigone lesion had a C→A transversion in codon 281. This mutation results in the substitution of a threonine for proline in the p53 protein. The right ALV tumor contained a G→C transversion in codon 281, resulting in an asparagine to histidine substitution (FIG. 2). The dysplastic lesion from the anterior floor of mouth was found to have a wild-type p53 sequence. The recurrent right ALV tumor was found to contain the identical 281 mutation seen in the original ALV tumor six months earlier (FIG. 2).

Evaluation of Tumor Margins

Figure 3:
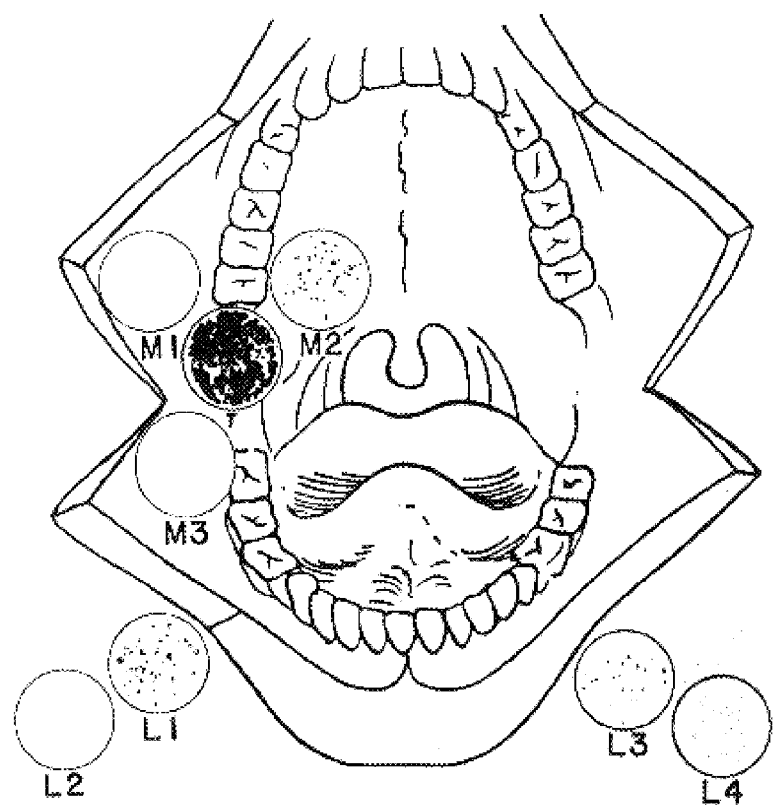
FIG. 3 is a schematic representation of molecular analysis of p53 mutations in tumor, margins, and nodes. In each sample, a portion of the p53 gene was amplified, cloned, and probed with a mutant-specific oligomer. Clones containing DNA with the ALV "signature" mutation at codon 281 hybridized with the nucleotide hybridization probe are visible as dots. Primary ALV tumor (T) produces many hybridized plaques, and a significant number are present in the histologically negative posterior margin ($M_2$) and bilateral histologically positive lymph nodes ($L_1$ and $L_3$. Two other marginal samples ($M_1$ and $M_3$) and histologically negative nodes ($L_2$ and $L_4$) were negative by molecular analysis.

Three separate margins surrounding each tumor were obtained at the time of the initial surgery and at resection of the recurrent tumor. DNA from each margin was separately analyzed for the presence of mutant sequences using the two mutant-specific probes. All margins were free of cells containing the codon 278 mutation found in the left RMT lesion. The codon 281 probe for the right ALV tumor identified malignant cells in one histologically negative mucosal margin taken from the right alveolar ridge posteromedial to the clinically detectable tumor (FIG. 3). Evaluation of the number of phage plaques containing the mutant sequence indicated that this margin contained approximately 28% malignant cells (70 positive plaques of 250 total plaques, Table 2). Microscope reassessment of a parallel section from the margin block confirmed it to be histologically negative for tumor when reviewed after the molecular analysis.

Surgical margins from the tumor that recurred six months later were again histologically negative for cancer cells. Samples from three areas were analyzed for the presence of mutant p53 sequences. Mutant cells were detected in only one margin from the posterior buccal region. Cancer cells comprised only 1 in 1,500 normal cells in this margin (Table 3).

Evaluation of Cervical Lymph Nodes

The p53 gene from two left-sided and seven right-sided cervical lymph nodes was amplified and cloned. Two of these nodes, one from each side, were histologically positive for tumor involvement. Probing all nine nodes for the codon 278 mutation demonstrated the absence of metastatic cells from the left RMT lesion. The histologically positive node from each side contained cells with the codon 281 mutation, indicating that the right ALV lesion had metastasized bilaterally. Eleven percent of the plaques from the right neck node and five percent from the left contained the mutated segment, providing an estimate of the extent of metastatic involvement in each node. All of the histologically negative nodes were also negative by molecular analysis for mutation at either codon (Table 3).

Evaluation of Exfoliated Cells in Oral Swabs

Prior to the resection of the recurrent tumor, the oral cavity was swabbed, first with a gloved finger and then with a tongue blade. The glove and tongue blade were then rinsed with saline into separate containers. Probing of PCR cloned products demonstrated the codon 281 mutation in 10% of cells from the glove swab and in 5% from the tongue blade scraping (Table 3).

TABLE 3

| Tumor | Designation | Tissue | Ratio |
|---|---|---|---|
| Primary | | | |
| 281 GAC-CAC | $M_1$ | R Posterior (−) | neg |
| | $M_2$ | R Post Alv. Ridge (−) | 28% |
| | $M_3$ | R Anterior (−) | neg |
| | $L_1$ | R LN (+) | 11% |
| | $L_3$ | L LN (+) | 5% |
| | $L_2$ | R LN (−) | neg |

TABLE 3-continued

| Tumor | Designation | Tissue | Ratio |
|---|---|---|---|
| | L₄ | L LN (−) | neg |
| | | R LN (−) | neg |
| | | L LN (−) | neg |
| Recurrent | | Anterior Deep (−) | |
| 281 GAC-CAC | | Posterior Deep (−) | neg |
| | | Posterior Buccal Mucosa (−) | neg |
| | | Saliva (blade) | .067% |
| | | Saliva (glove) | 5% |
| | | | 10% |

Molecular analysis of right (R) or left (L) alveolar ridge (ALV) tumor, margins (M) saliva, and lymph nodes (L) or (LN). Negative (−) and positive (+) by histopathology. Ratio denotes percent of tumor cells by molecular analysis. Positive analysis of saliva corresponded with recurrence of tumor.

The case presented in this example illustrates the clinical utility of molecular analysis of p53 mutations in HNSCC, as described in the present invention. The patient presented with multiple mucosal lesions, including two large invasive cancers and a small area of leukoplakia. Histologically, the two invasive tumors looked similar. They were well demarcated and the intervening mucosa of the hard palate appeared clinically and histologically normal. When DNA from the three lesions was extracted and amplified and the p53 gene was sequenced, each invasive tumor revealed a unique mutation. The presence of differing p53 mutations in the two tumors this case comports with previous identification of discordant p53 mutations in multiple primaries of HNSCC (Chung K Y, et al., *Cancer Res.*, 53:1676–1683, 1993).

Example 3 p53 Gene Mutations

Surgically resected specimens of invasive HNSCs were collected with consent from patients at Johns Hopkins Hospital. Tumors were fresh frozen and later carefully cryostat-microdissected to enrich for neo plastic cells. Cases with less than 50% neoplastic cells were not included in the analysis. More than fifty 12 micron sections were cut and placed in SDS/Proteinase K followed by extraction with phenol/chloroform and ethanol precipitation. Archival lesions consisting of dysplasia or carcinoma in situ (CIS) were identified retrospectively (1991–1993) through a systematic search in the files of the surgical pathology division of the Department of Pathology. These formalin-fixed, paraffin-embedded lesions were microdissected to enrich for neoplastic cells and then deparaffinized in xylene. DNA from tissue was then digested, extracted, and precipitated with ethanol as above.

From primary fresh frozen tumor DNA, a 1.8 kb segment of the p53 gene encompassing exons 5 to 9 was amplified by the polymerase chain reaction (PCR) as described in Example 1. A UDP cloning site was added to the 5' end of the primers (a=5'-CAUCAUCAUCAUUTCACTTGTGCCCTGACTT-3' (SEQ ID NO. 76) and d=5'-CAUCAUCUACUACTGGAAACTTTCCACTTGAT-3') (SEQ ID NO. 77) to allow cloning into a Cloneamp (BRL, Gaithersberg, Md.) plasmid vector (pSPORT) (Buchman, G. W., et al., *Focus*, 14:41–45, 1992). From archival samples the p53 gene was amplified in two segments. One segment included exons 5 and 6 utilizing primers "a" and b=5'-CUACUACUACUACCACTGACAACCACCCTT-3' (SEQUENCE ID NO. 78) and the other segment included exons 7 and 8 utilizing primers c=5'-CAUCAUCAUCAUCCAAGGCGCACTGGCCTC-3' (SEQUENCE ID NO. 79) and "d". Following amplification with uracil-containing primers, the PCR products were extracted with phenol/chloroform and run on a 1% agarose gel. The product was extracted from the gel, treated with I unit of uracil DNA glycosolase (UDG), and ½ the total product was annealed to the plasmid vector according to the manufacturer's instructions (Buchman, G. W. et al., supra.). Competent DH5-alpha cells were transfected with plasmid by heat shock, plated on ampicillin plates, and incubated overnight at 37°. More than 100 colonies were pooled, and plasmid DNA was isolated by alkaline lysis.

Sequencing

Double-stranded DNA obtained from plasmid was sequenced by the dydeoxy method utilizing Sequenase (United States Biochemical, Cleveland, Ohio) $^{33}$P-dATP or $^{35}$S-dATP (Sidransky, D., et al., *Science*, 252:706–709, 1991). Prior to termination, a 30 minute incubation with 0.5 units of Kenow fragment (USB) was added to eliminate "stop" bands. Sequencing reaction products were then separated on a 8M ureal 6% polyacrylamide gel and exposed to film. All mutations were confirmed by a second PCR reaction followed by recloning and resequencing.

Clinical Data

All information was obtained from patient records and assessed as follows.

Tobacco Exposure

Heavy=>1 pack/day

Moderate=<1 pack/day or quit 5–20 years ago

Mild=nonsmoker or quit>20 years ago

Alcohol Exposure

Light=nondrinker, quit>20 years ago, or special occasions only

Moderate=<12 ounces/week or quit 5–20 years ago

Heavy=>12 ounces/week

Results

To determine the relative timing of p53 gene mutations in HNSCC, 65 fresh primary invasive tumor samples and 37 archival preinvasive lesions were sequenced. Nineteen percent (7/37) of the early preinvasive lesions contained p53 mutations, compared to 43% (28/65) of the primary invasive HNCS, (Table 4). Only seven p53 mutations were found in preinvasive lesions: 5/24 in CIS lesions (21%) and 2/13 in dysplastic lesions (15%). Both of the latter mutations were in lesions of severe dysplasia; no lesions of mild or moderate dysplasia contained p53 mutations. The difference in incidence of p53 mutations between noninvasive and invasive lesions was found to be statistically significant (p<0.02 by chi-squared analysis).

Closer analysis of the specific p53 mutations found in all lesions reveals that 72% (26/36) were missense mutations and 28% (10/36) would produce truncated proteins. This represents a high percentage of mutations resulting in truncations, similar to that seen in esophageal cancer (Hollstein, M., et al., 253:49–53, 1991). Of these, four were nonsense mutations, five were frame shift mutations and one was an altered splice site mutation.

Figures 4A, 4B:
FIG. 4A shows a sequencing gel audioradiograph from 6 invasive tumor DNA samples with lanes grouped together for rapid identification of novel bands upon visual comparison. Arrow points to T→C mutation (codon 220) in lane 1 from the tumor of Patient H17 (Table 4).
FIG. 4B shows the sequencing gel and the arrow points to C→T mutation (codon 146) in the tumor DNA of Patient C2 with CIS (Table 4).

Interestingly, one of these mutations (H18) was a deletion that occurred near small repeating sequences, perhaps secondary to replication errors as described in Jejo, N., et al., (*Oncogene*, 8:209–213, 1993). Additionally, one tumor (H15) contained an unusual pyrimidine dimer 2 bp mutation at codon 245. Although common in UV-induced skin tumors similar mutations have been previously seen in bladder cancer and may also be induced by reactive oxygen free radicals or severe exposure to carcinogens (Spruck, C. H., et at., *Can. Res.*, 53:1162–1166, 1993). Eighty-two percent of the invasive tumors (23/28) had lost the wild type allele, suggesting loss of the remaining p53 allele during tumor progression. One tumor (H10) contained two point mutations, and analysis of individual clones revealed that each occurred on a different allele. In contrast, 5/7 p53 mutations in early lesions appeared to have retained of the wild type allele. The presence of this allele may represent some residual contamination from surrounding non-neoplastic tissue, or it may mean that the second allele had not yet been lost in these early lesions. Mutations were spread over a wide range of codons yet occurred in the most highly conserved regions of p53 (FIG. 4A and 4B) as previously reported (Hollstein, M., et al., supra.). The mutations also occupied a spectrum similar to that seen in SC carcinoma of the lung (Y. Kishimoto et al., *Can. Res.* 52:4799–4804, 1992), but they differed from mutations seen in other epithelial tumors.

Clinical data were available for 26 of the 27 patients with primary invasive carcinomas containing mutations in the p53 gene (Table 4). Of these, 16/25 point mutations (64%) were at guanine nucleotides, including 8 G→A, 5G→T, or 3G→C changes often associated with benzopyrenes, nitrosamines, and possibly oxygen radicals from cigarette smoke (Kishimoto, Y., et al., *Can. Res.*, 52:4799–4804, 1992; Puisieux, A., et al., *Can. Res.*, 51:6185–6189, 1991; Ames, B. N., *Science*, 221:1256–1264, 1983; Kalra, J., et al., *Int. J. Exp. PalthoL*, 72:1–7, 1991). Thirteen of these 16 patients were heavy smokers, and five of them also had histories of heavy drinking. Only one patient with a G→A transition was a nonsmoker and nondrinker. Overall, 25 of 26 patients with mutations had histories of moderate to heavy smoking. In contrast, eleven of 38 patients without p53 mutations had had only minimal exposure to tobacco and alcohol. Although the exact amount was quite variable and difficult to quantify accurately, carcinogen exposure was significant in all but one of the patients with missense mutations. Exposure was particularly heavy in the group with specific mutations previously found to be associated with known carcinogens in cigarette smoke. The presence or absence of p53 mutations did not correlate with age or sex of the patient nor with the site, size, or stage of the tumor.

One patient (H27) had two separate tumors on opposite sides of the oral cavity (Table 4). Each tumor had a distinct p53 mutation as previously seen in patients with separate primaries (Chung, K.Y., et al., *Can. Res.*, 53:1676–1603, 1993). One lesion from another patient (C7) with a G→A transition was a nonsmoker and nondrinker. Overall, 25 of 26 patients with mutations had histories of moderate to heavy smoking. In contrast, eleven of 38 patients without p53 mutations had had only minimal exposure to tobacco and alcohol. Although the exact amount was quite variable and difficult to quantify accurately, carcinogen exposure was significant in all but one of the patients with missense mutations. Exposure was particularly heavy in the group with specific mutations previously found to be associated with known carcinogens in cigarette smoke. The presence or absence of p53 mutations did not correlate with age or sex of the patients nor with the site, size, or stage of the tumor. Clinical data were not available for patients with noninvasive (dysplastic or CIS) lesions.

Figure 5:
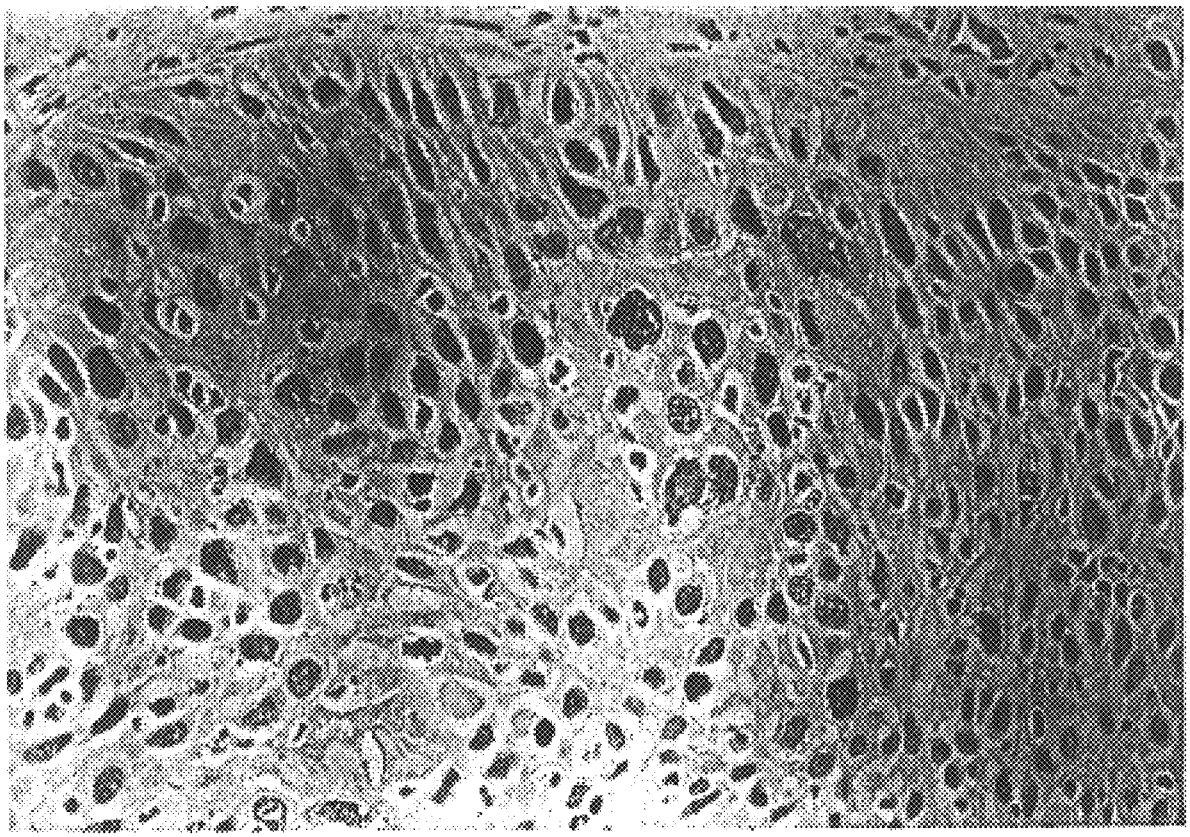
FIG. 5 shows immunohistochemical staining of p53 demonstrating intense nuclear staining in the carcinomatous portion of a carcinoma arising in an inverted papilloma from Patient C7 (Table 4). The inverted papilloma portion did not stain. The staining was performed using the CM-1 polyclonal anti-p53 antibody and the ABC VectaStain® kit (Vector Laboratories).

As shown in FIG. 5, only the carcinomatous portion of the neoplasm stained with an anti-p53 antibody (indicative of p53 mutation) and the ABC VectaStain® kit (Vector Laboratories) (Cunningham, J., et al., *Can. Res.*, 52:1974–1980, 1992). Microdissection of the distinct histologic regions followed by DNA extraction and p53 sequencing revealed a codon 175 mutation in the carcinoma, while no mutations were detected in the papilloma. This case was stained simply to illustrate the histopathologic progression to cancer associated with a new p53 mutations.

Table 5 lists the known p53 mutations associated with head and neck tumors.

TABLE 4A

PRIMARY INVASIVE HNSC TUMORS WITH P53 MUTATIONS

|     | STAGE | TOB/ETOH | SITE | AGE | SEX | CODON | MUTATION | AMINO ACID |
| --- | --- | --- | --- | --- | --- | --- | --- | --- |
| H1  | T2N0 | H/M | L | 41 | M | 275 | TGT→TAT | CYS→TYR |
| H2  | T3N0 | H/L | L | 67 | F | 296 | CAC→CCC | HIS→PRO |
| H3  | T3N0 | M/M | L | 80 | M | 163 | TAC→CAC | TYR→ASP |
| H4  | T3N25 | H/H | L | 65 | M | 175 | CGC→CAC | ARG→HIS |
| H5  | T2N2 | H/H | OP | 36 | M | 296 | GAG→TAG | GLU→TERM |
| H6  | T2N0 | H/H | OP | 55 | F | 234 | TAC→TCC | TYR→CYS |
| H7  | T4N2C | H/H | OP | 55 | M | 278 | T insertion | FS |
| H8  | T3N0 | H/L | L | 58 | M | 228 | GAC→GAG | ASP→GLU |
| H9  | N/A | N/A | L | N/A | N/A | 296 | GAG→TAG | GLU→TERM |
| H10 | T1N0 | H/L | HP | 59 | M | 175 | CGC→CAC | ARG→HIS |
|     |     |     |   |    |   | 216 | GTG→ATC | VAL→MET |
| H11 | T2N1 | H/H | OC | 68 | M | * | acceptor G→T | SPLICE SITE |
| H12 | T3N1 | M/H | OC | 84 | M | 220 | TAT→TCT | TYR→SER |
| H13 | T3N1 | H/L | L | 64 | M | 198 | GAA→AAA | GLU→LYS |
| H14 | T1N0 | M/H | OC | 65 | M | 205 | TAT→GAT | TYR→ASP |
| H15 | T1N1 | M/H | OC | 68 | F | 245 | GGC→GTT | GLY→VAL |
| H16 | T2N0 | H/L | L | 68 | F | 257 | CTG→CCG | LEU→PRO |
| H17 | T2N2A | H/H | L | 46 | M | 220 | TAT→TGT | TYR→CYS |
| H18 | T2N0 | H/H | OC | 64 | F | 257-61 | 9bp deletionFS |  |
| H19 | T3N0 | H/H | OP | 70 | F | 278 | CCT→TCT | PRO→SER |
| H20 | T2N0 | H/M | OP | 46 | M | 220 | TAT→TGT | TYR→CYS |
| H21 | T4N2C | H/M | L | 47 | M | 279 | G insertion | FS |
| H22 | T4N0 | L/L | OC | 85 | F | 248 | CCG→CAG | ARG→GLN |
| H23 | TxN2 | H/M | NE | 61 | M | 237 | ATG→ATT | MET→ILE |
| H24 | T3N2C | H/H | L | 58 | M | 251 | ATC→AAC | ILE→ASN |

TABLE 4A-continued

PRIMARY INVASIVE HNSC TUMORS WITH P53 MUTATIONS

| | STAGE | TOB/ETOH | SITE | AGE | SEX | CODON | MUTATION | AMINO ACID |
|---|---|---|---|---|---|---|---|---|
| H25 | T2N2C | H/NA | L | 66 | M | 230 | TAC→TAA | TYR→TERM |
| H26 | T2N0 | H/L | OC | 50 | F | 273 | CGT→GGT | ARG→GLY |
| H27A | T3N0 | H/H | OC | 58 | F | 278 | CCT→ACT | PRO→THR |
| | 14N2C | H/H | OC | 58 | F | 281 | GAC→CAC | ASP→HIS |

Tob = Tobacco; ETOH = Ethanol; L = Light; M = Moderate; H = Heavy; N/A = Not Available
FS = Frame Shift; L = Larynx; OP = Oropharynx; OR = Oral Cavity; NE = Neck
*Intron 5 (−3bp from exon 6).
For assessment of tobacco and ETOH exposure see Example 3 text.

TABLE 4B

NONINVASIVE TUMORS

| | PATHOLOGY | SITE | CODON | MUTATION | AMINO ACID |
|---|---|---|---|---|---|
| C1 | CIS | OC | 200 | A deletion | FS |
| C2 | CIS | OC | 148 | TGG→TGA | TRP→TERM |
| C3 | dys | OC | 249 | A insertion | FS |
| C4 | dys | OC | 169 | ATG→ACG | MET→THR |
| C5 | CIS | OC | 278 | CCT→ACT | PRO→THR |
| C6 | CIS | OC | 168 | CGC→TGC | ARG→CYS |
| C7 | CIS | OC | 176 | TGC→TTC | CYS→PHE |

Tob = Tobacco; ETOH = Ethanol; L = Light; M = Moderate; H = Heavy; N/A = Not Available
FS = Frame Shift; L = Larynx; OP = Oropharynx; OC = Oral Cavity; NE = Neck
*Intron 5 (−3bp from exon 6).
For assessment of tobacco and ETOH exposure see Example 3 text.

TABLE 5

P53 MUTATIONS IN HEAD AND NECK TUMORS

| Codon | Base pair change |
|---|---|
| 126 | tac-tag |
| 132 | aag-agg |
| 146 | tgg-tga |
| 148–151 | 10 bp deletion FS |
| 154 | 1 bp deletion FS |
| 155 | acc-ccc |
| 158 | cgc-tgc |
| 163 | tac-cac |
| 169 | atg-acg |
| 173 | gtg-ctg |
| 175 | cgc-cac |
| 176 | tgc-ttc |
| 176 | tgc-ttc |
| 179 | cat-cgt |
| 198 | gaa-aaa |
| 200 | a deletion FS |
| 203 | 1 bp deletion FS |
| 205 | tat-gat |
| 205 | tat-tct |
| 205 | tat-tgt |
| 205 | tat-tgt |
| 209 | 2 bp deletion FS |
| 213 | cga-tga |
| 213 | cga-cgg |
| 213 | cga-tga |
| 216 | gtg-atg |
| 216 | gtg-ttt |
| 220 | tat-tgt |
| 220 | tat-cat |
| 220 | tat-tct |
| 228 | gac-gag |
| 234 | tac-tgc |
| 236 | tac-taa |
| 237 | atg-att |

TABLE 5-continued

P53 MUTATIONS IN HEAD AND NECK TUMORS

| Codon | Base pair change |
|---|---|
| 237 | atg-ata |
| 238 | tgt-tat |
| 238 | tgt-ttt |
| 242 | tgc-ttc |
| 245 | ggc-gtt |
| 245 | ggc-gac |
| 245 | ggc-tgc |
| 246 | atg-ttg |
| 248 | cgg-tgg |
| 248 | cgg-ctg |
| 248 | cgg-tgg |
| 248 | cgg-tgg |
| 248 | cgg-cag |
| 248 | cgg-ctg |
| 249 | agg-ggg |
| 249 | agg-agt |
| 249 | a insertion FS |
| 251 | atc-aac |
| 257 | ctg-ccg |
| 257–61 | 9bp deletion |
| 266 | gga-gaa |
| 271 | 1 bp deletion FS |
| 273 | cgt-ggt |
| 273 | cgt-cat |
| 275 | tgt-tat |
| 278 | t insertion FS |
| 278 | cct-tct |
| 278 | cct-act |
| 278 | cct-cgt |
| 278 | cct-act |
| 279 | g insertion |
| 279 | ggg-gag |
| 281 | gac-cac |
| 281 | gac-gag |
| 281 | gac-cac |
| 285 | gag-aag |
| 286 | gaa-aaa |
| 289–290 | 2 bp (tt) addition FS |
| 294 | gag-tag |
| 296 | cac-ccc |
| 298 | gag-gca |
| 298 | gag-tag |
| 298 | gag-tag |
| 305–306 | taag insertion |
| 307 | 16 bp deletion FS |
| Intron 5 | acceptor g-t |

FS = Frame Shift

Example 4

Additional Case Studies

Invasive head and neck squamous carcinomas were surgically resected at Johns Hopkins Hospital and portions of the neoplasms were collected with the consent of the patient.

After the primary tumor was removed and the margins were sampled by frozen section to confirm the adequacy of resection, additional normal appearing tissue was taken from the edges of the surgical defect. Also, portions of lymph nodes from neck dissection specimens that were not used for diagnostic histopathology were fresh frozen. The DNA was prepared from al tissues as described in Example 1 and by Sidransky, et al., (*Science*, 252:706, 1991).

A. METHODS

1. Histopathologic Exam

Portions of the primary carcinomas, surgical margins, and lymph nodes were processed and sectioned in an identical manner to guarantee accurate histopathologic assessment before molecular analysis was performed. The frozen specimens were embedded in OCT (Tissue Tek, Elkhart, Ind.), a polyglycol embedding medium, and the frozen specimen block was evenly planed with a cryostat, resulting in a smooth surface for sectioning. First, two 5-micron thick sections were taken for hematoxylin and eosin (H&E) staining and examination by light microscopy. The slides were read as negative, suspicious, or positive for the presence of squamous carcinoma. Next, twenty 12-micron sections were cut and placed in SDS/Proteinase K for DNA analysis. The tissue DNA was extracted with phenol/chloroform and precipitated with ethanol as described (Boyle, J, Hakim J, Koch W, et al., *Can. Res.*, 53:4477–80, 1993). A second set of two H&E sections was taken, followed by a second set of 12-micron sections for DNA analysis, and then a third set of H&E sections. Two hundred and forty microns of tissue for DNA analysis was, therefore, immediately sandwiched between sections examined by light microscopy.

2. p53 Gene Sequencing

A 1.8 kb fragment of the p53 gene encompassing exons five to nine was amplified from the fresh-frozen primary tumor DNA by the polymerase chain reaction (PCR) as described in Example 1 and Sidransky, et al., 1991, supra and Boyle J, et al., supra. A UDP cloning site was added to the 5' end of the primers and the DNA was cloned into a CloneAmp (Gibco/BRL) plasmid vector. Competent DH5-alpha cells were then transfected with plasmids using the heatshock method (Buchman G W., et al., *Focus*, 14:41–45, 1992). The transformed cells were plated on ampicillin plates and incubated at 37° C. overnight. Colonies were pooled and plasmid DNA was extracted by alkaline lysis. The double-stranded DNA was sequenced by the dideoxy method, using $^{32}$P-dATP (New England Nuclear), Sequenase (USB), and klenow enzyme (NEB) (Boyle, et al., supra). The sequencing reactions were then electrophoreses on 8M ureal 6% polyacrylamide gels, fixed, and exposed overnight to film at room temperature.

3. Molecular Probing

The patients found to have p53 mutations in their primary HNSC were selected for further analysis. DNA extracted from the sectioned margins and lymph nodes was used to amplify exons five to nine of the p53 gene by PCR as described (Sidransky, D., et al., *Science*, 252:706–709, 1991; Sidransky, D., *Nature*, 355:846–847, 1992). The PCR products were then cloned into a bacteriophage vector and amplified further in *Escherichia coli* (Sidransky, D., et al., *Science*, 252:706–709, 1991). Between 500 and 10,000 clones were then transferred to nylon membranes and hybridized to $^{32}$P-end labeled oligonucleotide probes. These oligonucleotide probes were unique and specific for the mutant p53 base pair found in each patient's respective primary HNSC. Following hybridization, the membranes were washed stringently at 54–60° C. to detect only mutant-specific binding. The membranes were then exposed to film and positive-hybridizing plaques identified the presence of a p53 mutant gene. The percentage of clonal (mutated) tumor cells in each specimen was estimated by counting the number of labeled plaques and dividing this number by the total number of plaques present on each plate that contained the inserted p53 DNA fragment (all plaques that hybridized to a wild-type p53 probe).

The assay was confirmed using positive and negative controls for each margin and lymph node examined. The positive control was the amplified p53 gene product derived from each respective primary carcinoma; it was detected by hybridization to its mutant-specific oligonucleotide prove. The negative control included "cloned" PCR products from reactions devoid of DNA and cloned p53 products derived from patients with a different p53 mutation in the primary tumor. All positive assays were repeated by reamplification, recloning, and reprobing.

B. RESULTS

1. Study Population

Forty seven patients with invasive HNSC who were scheduled for tumor resection at Johns Hopkins Hospital entered the study. Following sequencing of the primary tumor DNA, 21 patients (45%) were found to have p53 gene mutations in their neoplasms (Table 6). The 21 patients with p53 mutations consisted of 11 females and 10 males with an average age of 62 years (range was 46 years to 85 years). Twenty of 21 patients had significant tobacco use and 16 of the 21 patients had a history of heavy alcohol consumption. The patients most commonly presented with advanced-stage or recurrent squamous carcinoma of the head and neck.

Figure 6:
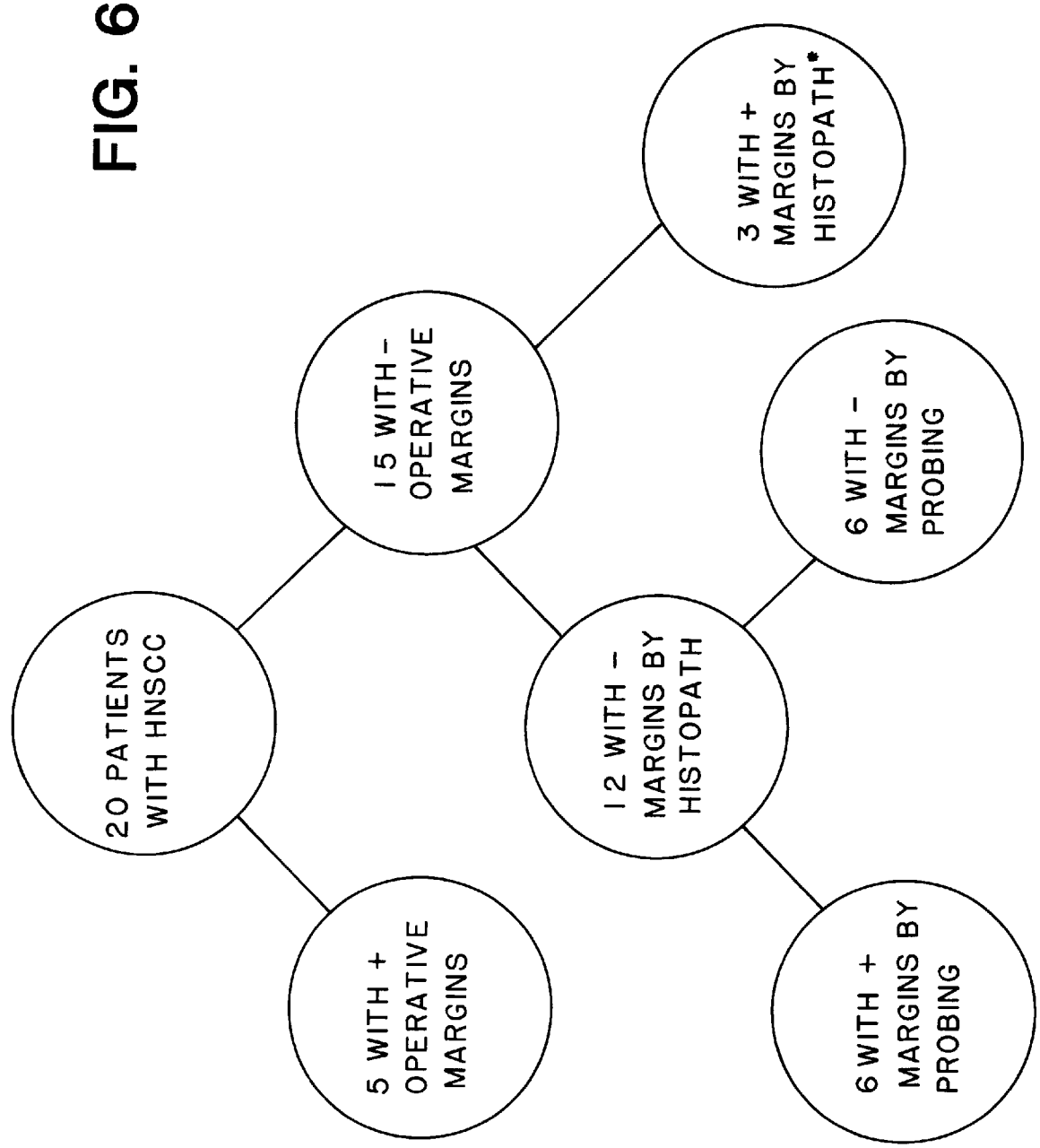
FIG. 6 shows a schematic illustration of the molecular analysis and histopathologic assessment of the surgical margins of head and neck squamous carcinoma patients with intended curative resections.

Sixteen of the 21 patients with p53 mutations had surgical margins, four had both surgical margins and lymph nodes, and one had only lymph node tissue available for further molecular analysis. A total of 56 margins from 20 patients (average of 2.8 margins/patient) and 27 cervical lymph nodes from five patients (average of 5.4 nodes/patient) were studied. Five patients had positive surgical margins in the operating room on final permanent histopathologic diagnosis and were excluded from further analysis. Fifteen of the 20 patients with surgical margins available for molecular analysis were found to have negative resection margins without evidence of microscopic carcinoma documented on the final pathology report from their HNSC operations (FIG. 6).

2. Surgical Margins

Figure 7A:
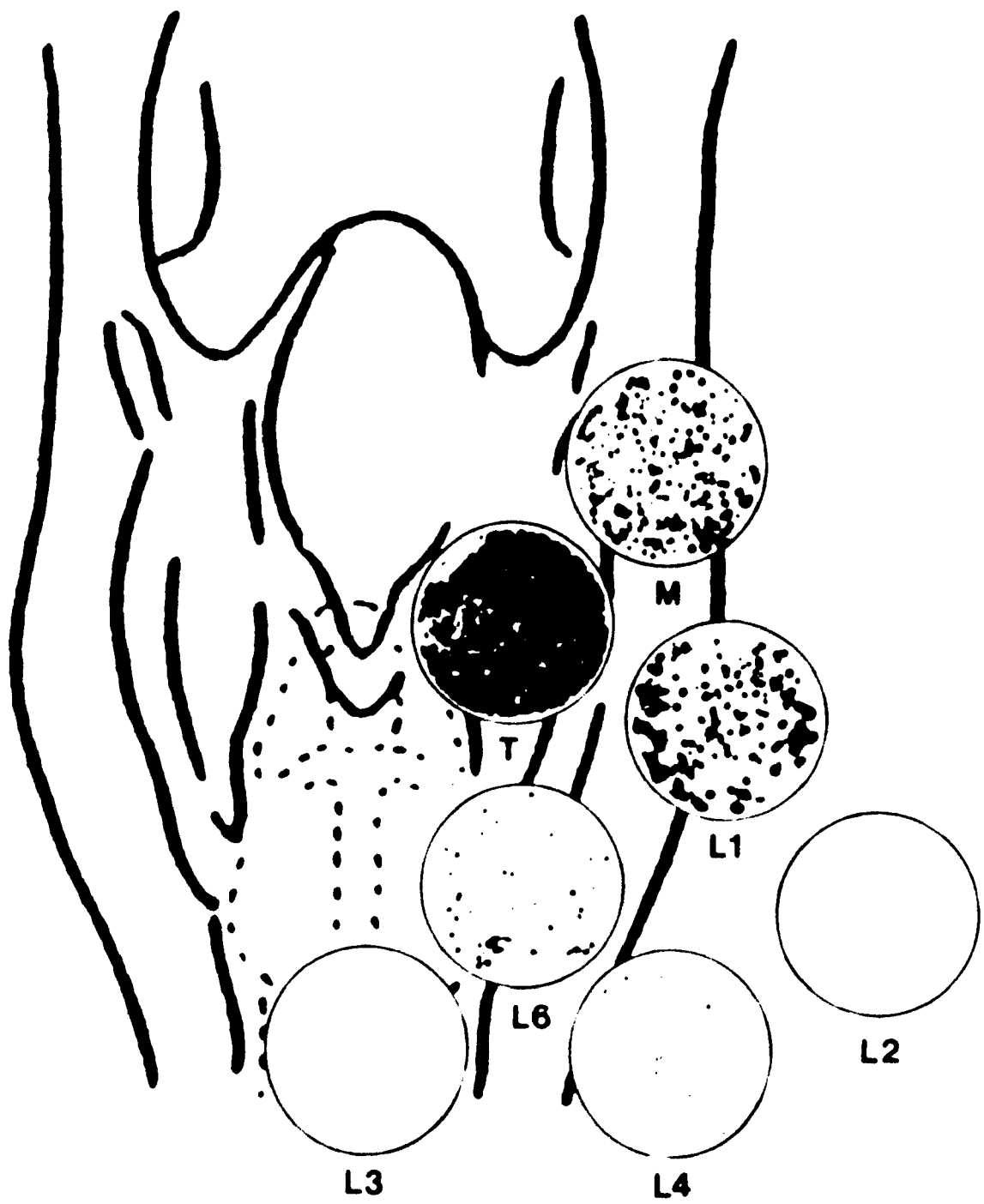
FIG. 7A (patient 4), shows that tumor cells are identified in one margin (M) and lymph nodes (L1, L4, and L6) with negative hybridization (empty circles) in L2 and L3.
Figure 7B:
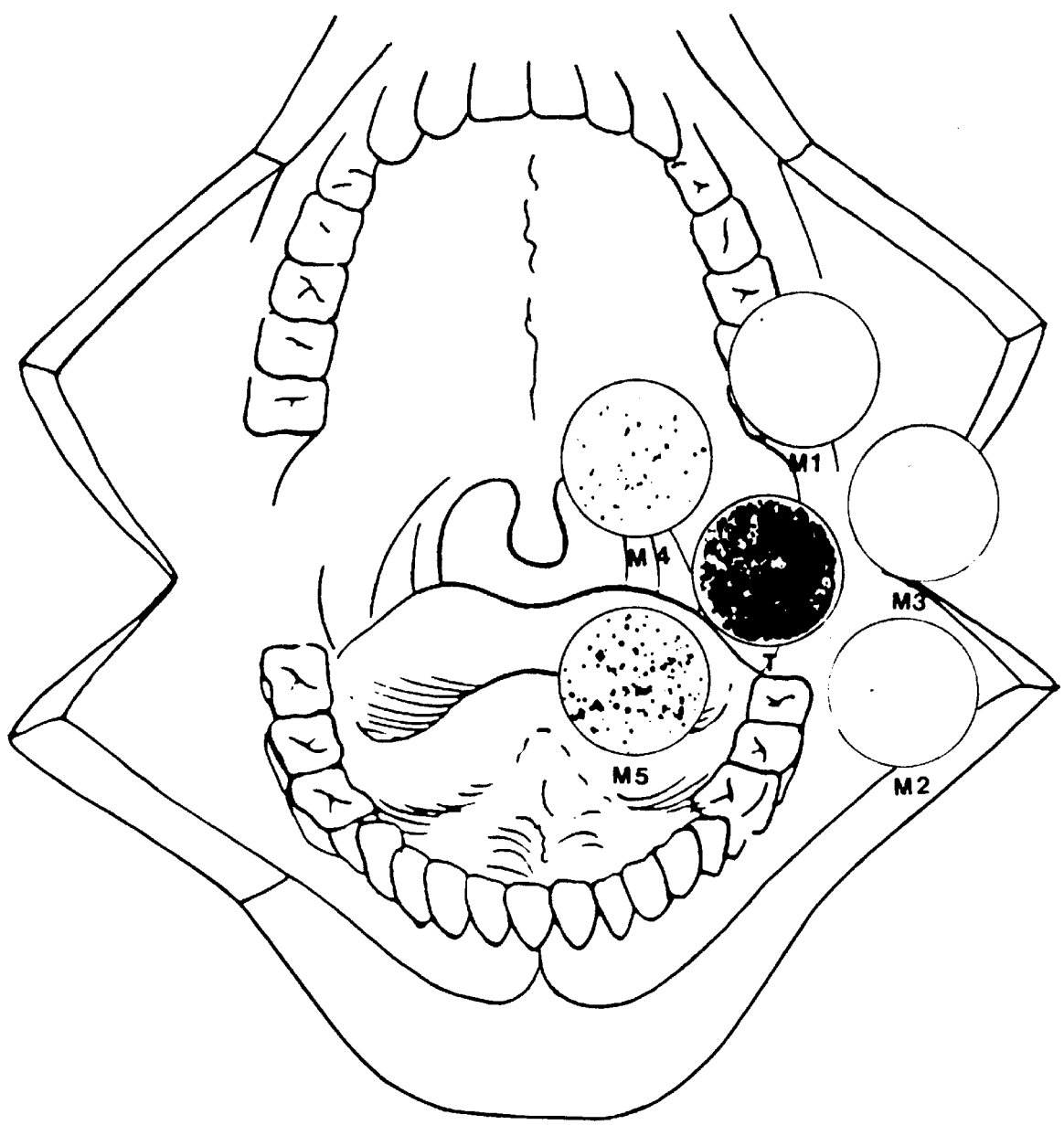
FIG. 7B (patient 9), shows that many tumor cells are present in M4 and M5 and fewer tumor cells in M1 and M2, with margin M3 free of tumor cells.
Figure 7C:
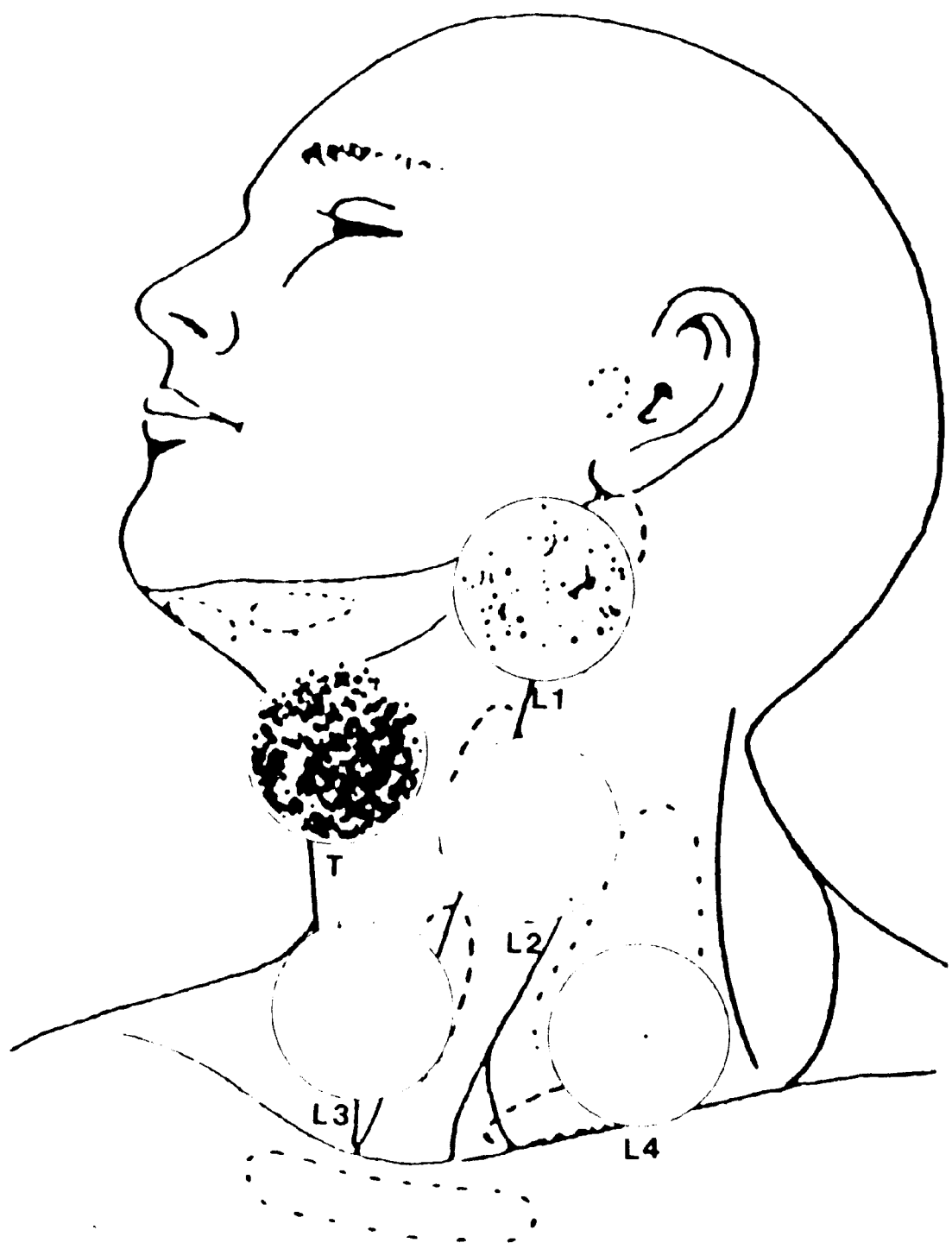
FIG. 7C (patient 16), shows that micrometastases are seen in all 4 lymph nodes (L1–L4) to varying degrees.

The "negative" surgical margins from the 15 patients described above were probed with the specific p53 mutant oligonucleotide derived from their primary tumors (Table 7). Nine of the 15 patients (60%) had at least one surgical margin that specifically hybridized to the mutant probe, thereby demonstrating the presence of mutation-containing neoplastic cells (FIGS. 7A–7C). FIG. 7 shows a molecular anlaysis of surgical margins and lymph nodes. Autoradiographs of plaque lifts hybridized with mutant-specific oligomers derived from each patient's tumor are shown. Positive (specific) hybridizing clones (black dots) are detected in surgical margins (M), in lymph nodes (L), and in the primary tumor (T) as a positive control.

FIG. 7A (patient 4), shows that tumor cells are identified in one margin (M) and lymph nodes (L1, L4, and L6) with negative hybridization (empty circles) in L2 and L3.

FIG. 7B (patient 9), shows that many tumor cells are present in M4 and M5 and fewer tumor cells in M1 and M2, with margin M3 free of tumor cells.

FIG. 7C (patient 16), shows that micrometastases are seen in all 4 lymph nodes (L1–L4) to varying degrees. Details of each patient in FIGS. 7A, B, and C, and percentage of tumor cells in margins and lymph nodes appear in Tables 7, 8, and 9.

Figure 8A:
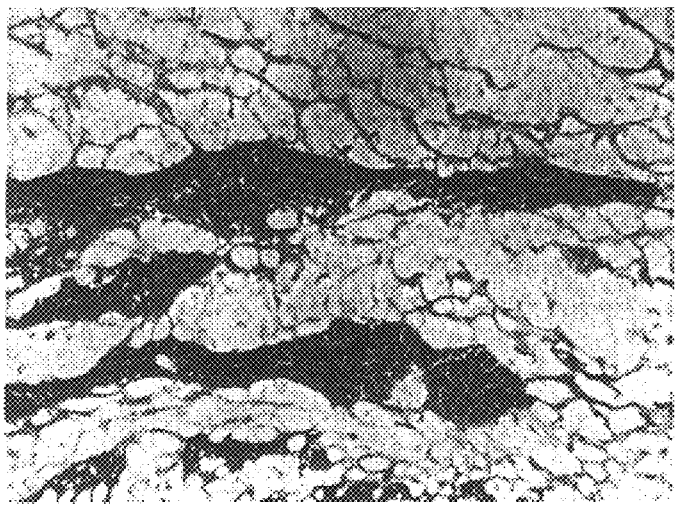
FIG. 8 shows a photomicrograph of histopathologic margins. Hematoxylin and eosin staining of positive (FIG. 8A), suspicious (FIG. 8B), and negative (FIG. 8C) surgical margins are demonstrated. All of the above margins had tumor cells detected by molecular analysis. The percentage of neoplastic cells was 10% in FIG. 8A (M2 from patient 13), 5% in FIG. 8B (M4 from patient 9), and 0.25% in FIG. 8C (M2 from patient 15). Details of each patient in FIGS. 8A, 8B, and 8C, and percentage of tumor cells in margins and lymph nodes appear in Tables 7, 8, and 9.
Figure 8B:
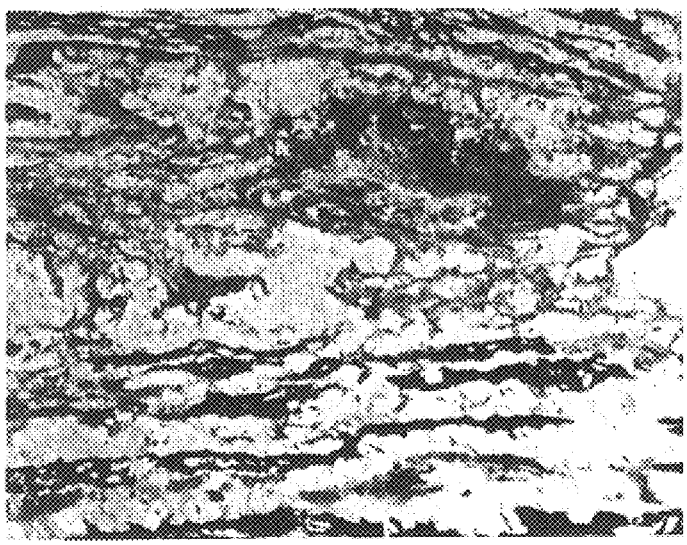
Figure 8C:

Review of the fresh-frozen surgical margins sent for molecular analysis revealed microscopic cancer in three of these nine patients (FIG. 6). Those surgical margins that were positive for squamous carcinoma based on light microscopy consistently demonstrated significant mutant-specific hybridization on molecular analysis (Table 7). The percentage of cells with mutations in the surgical margins ranged from 0.05% to 10.0% by molecular analysis. The positive margins diagnosed by histopathology consistently had at least 5.0% neoplastic cells by molecular probing. Conversely, when the percentage of cells harboring p53 mutations comprised less than 5.0% of the cell population in the surgical margins, they were not definitively detected by light microscopic examination of the H&E sections. The remaining six patients had margins that did not hybridize to the mutant -specific probes, suggesting that those surgical margins did not harbor neoplastic cells (FIG. 6). Representative sections from positive, suspicious, and negative margins by histopathologic assessment are shown in FIGS. 8A, 8B, and 8C, respectively. All three cases illustrated were positive by molecular analysis. FIG. 8 shown a photomicrographs of histopathologic margins. Hematoxylin and eosin staining of positive FIG. (8A), suspicious FIG. (8B), and negative FIG. (8C) surgical margins are demonstrated. All of the above margins had tumor cells detected by molecular analysis. The percentage of neoplastic cells was 10% in 8A (M2 from patient 13), 5% in 8B (M4 from patient 9), and 0.25% in 8C (M2 from patient 15).

3. Cervical Lymph Nodes

Sandwich sections of 27 cervical lymph nodes from five patients with HNSC were also carefully examined before molecular analyses were performed. Three of the five patients were diagnosed with one cervical lymph node positive for the presence of metastatic carcinoma by light microscopy (Table 8). Thus, three of the 27 lymph nodes had evidence of metastatic HNSC on standard histopathologic examination. In contrast, when the cloned DNA from the lymph nodes was probed with the respective p53 mutant-specific oligonucleofide derived from their primary tumor, positive hybridization was identified in nine of the 27 nodes from four of the 5 patients. Therefore, of the 24 lymph nodes negative by light microscopy, six (25%) were found by molecular analysis to contain neoplastic cells. Neoplastic cells comprised between 0.3% and 10.0% of the total cell population in these positive nodes (FIG. 7). As was true for the margins, the lymph nodes diagnosed as positive for HNSC by light microscopy all contained a population of at least 5.0% mutant cells (Table 8). Three of the four patients with occult metastases identified by probing would have had their head and neck cancers upgraded to a more advanced stage based on the molecular analysis.

Primary tumor from all 21 patients showed positive hybridization on southern blot analysis of p53 amplified PCR products derived from tumor DNA using their individually synthesized oligonucleotide probe (Sidransky, D., et al., *Science*, 256:102–105, 1992). The patients' samples also consistently demonstrated negative hybridization with an oligonucleotide probe derived from the sequence of a different p53 mutation.

4. Patient Survival

After a brief follow-up period (mean=6.4 months), 18 of the 21 patients studied were alive and three had succumbed to their cancer. Twelve of the surviving patients are currently disease-free, five have loco regional tumor recurrence, and one has distant metastatic disease. It is noteworthy that the location of the tumor margins positive by molecular analysis accurately predicted the site of local recurrence in two patients.

TABLE 6

CHARACTERISTICS OF PATIENTS WITH HNSC

| Patient # | Age/Sex | Site | Stage | p53 Mutation |
|---|---|---|---|---|
| 1 | 66/F | Larynx | T3NoMo | 257 CTG-CCG |
| 2 | 59/M | Larynx | T1NoMo(R) | 175 CGC-CAC |
| 3 | 66/F | opx | T3N1Mo(R) | 245 CCG-CTT |
| 4 | 46/M | Hypopx | T2N2aMo | 220 TAT-TGT |
| 5 | 49/M | opx | T3NoMo | 275 TGT-TAT |
| 6 | 54/F | opx | T2NoMo | 257 9BP Del |
| 7 | 66/M | opx | T3N2aMo | 187 GGT-GAT |
| 8 | 51/M | Hypopx | T4N1Mo | 193 CAT-CGT |
| 9 | 63/M | opx | T3N2bMo | 306 CGA-TGA |
| 10 | 35/F | oc | T4NoMo | 248 CGG-GGG |
| 11 | 56/M | Hypopx | T4N1Mo | 255 ATC-TTC |
| 12 | 62/F | opx | T1N1Mo | 278 CCT-CGT |
| 13 | 56/F | Hypopx | T4N2Mo | 298 GAG-TAG |
| 14 | 57/M | Larynx | T2NoMo(R) | 228 GAC-GAG |
| 15 | 59/M | opx | T4N2bMo | 220 TAT-TGT |
| 16 | 65/M | Hypopx | T3N2bMo | 175 CGC-CAC |
| 17 | 68/F | Larynx | T1NoMo(R) | 272 GTG-GAG |
| 18 | 67/M | Larynx | T3NoMo | 253 ACC-TCC |
|  |  |  |  | 254 ATC-TTC |
| 19 | 73/F | Larynx | T2NoMo(R) | 180 GAG-TAG |
| 20 | 72/F | oc | T1NoMo(R) | 249 AGG-GGG |
| 21 | 62/F | opx | T4N3Mo | 213 CGA-TGA | opx = Oropharyngeal
Hypopx = Hypopharynx
oc = Oral Cavity
(R) = Recurrent Tumor

TABLE 7

MOLECULAR ANALYSIS OF SURGICAL MARGINS

| Patient # | Surgical Margins | Histopath. Exam | Mutant-specific Probing | Mutant Clones (%) |
|---|---|---|---|---|
| 1 | M1 | Neg. | Pos. | 0.35% |
|  | M2 | Neg. | Pos. | 0.5% |
|  | M3 | Neg. | Neg. | — |
|  | M4 | Neg. | Pos. | 0.1% |
|  | M5 | Neg. | Pos. | 0.2% |
|  | M6 | Neg. | Pos. | 0.5% |
| 2 | M1 | Neg. | Pos. | 0.1% |
|  | M2 | Neg. | Pos. | 0.25% |
|  | M3 | Neg. | Pos. | 0.05% |
|  | M4 | Neg. | Pos. | 0.2% |
| 3 | M1–M2 | Neg. | Neg. | — |
| 4 | M1 | Neg. | Pos. | 5.0% |
| 5 | M1–M3 | Neg. | Neg. | — |
| 6 | M1–M3 | Neg. | Neg. | — |
| 7 | M1–M2 | Neg. | Neg. | — |
| 8 | M1 | Neg. | Neg. | — |
|  | M2 | Neg. | Pos. | 4.0% |
| 9 | M1 | Neg. | Pos. | 0.2% |
|  | M2 | Neg. | Pos. | 0.5% |
|  | M3 | Neg. | Neg. | — |
|  | M4 | Suspic. | Pos. | 5.0% |
|  | M5 | Pos. | Pos. | 10.0% |
| 10. | M1 | Neg. | Pos. | 0.4% |
|  | M2 | Neg. | Pos. | 1.3% |
| 11 | M1–M2 | Neg. | Neg. | — |
|  | M3 | Suspic. | Pos. | 0.2% |
|  | M4 | Suspic. | Pos. | 0.7% |
| 12 | M1 | Neg. | Neg. | — |
|  | M2 | Neg. | Neg. | — |
| 13 | M1 | Neg. | Neg. | — |
|  | M2 | Pos. | Pos. | 10.0% |
| 14 | M1–M8 | Neg. | Neg. | — |
| 15 | M1 | Neg. | Neg. | — |

TABLE 7-continued

MOLECULAR ANALYSIS OF SURGICAL MARGINS

| Patient # | Surgical Margins | Histopath. Exam | Mutant-specific Probing | Mutant Clones (%) |
|---|---|---|---|---|
| | M2 | Neg. | Pos. | 0.25% |

Each consecutive letter indicates a separate surgical margin. Histopathologic exam was performed by staff surgical histopathologists, and the slides were read as positive ("Pos."), suspicious ("Suspic."), or negative "Neg.") for squamous cell carcinoma. Forty percent mutant clones is equal to number of mutant-specific clones/total clones with p53 insert (see text).

TABLE 8

MOLECULAR ANALYSIS OF CERVICAL LYMPH NODES

| Patient # | Cervical Nodes | Histopath. Exam | Molecular Probing | Percent Mutant Clones |
|---|---|---|---|---|
| 1 | L1 | Positive | Positive | 10.0% |
| 2 | L1–L10 | Negative | Negative | — |
| | L11 | Negative | Positive | 0.35% |
| 3 | L1–L3 | Negative | Negative | — |
| 4 | L1 | Positive | Positive | 10.0% |
| | L2–L3 | Negative | Negative | — |
| | L4 | Negative | Positive | 1.0% |
| | L5 | Negative | Negative | — |
| | L6 | Negative | Positive | 2.0% |
| | L7–L8 | Negative | Negative | — |
| 16 | L1 | Positive | Positive | 5.0% |
| | L2 | Negative | Positive | 0.4% |
| | L3 | Negative | Positive | 0.3% |
| | L4 | Negative | Positive | 0.7% |

Each consecutive letter represents a separate cervical lymph node. The slides were read as positive, suspicious, or negative for squamous cell carcinoma.

The results shown in these examples provide an embodiment wherein successful detection of neoplasia was accomplished and provides a practical basis for a new approach for detecting the presence of neoplasias, such as in histologic margins and regional lymph nodes. The approach would have utility in monitoring patient populations and treatments designed to minimize the incidence of neoplasia. It also could be used in screening asymptomatic patients, especially those at risk by virtue of inherited or environmental factors, such as tobacco and alcohol consumption, for the presence of neoplasia. The current results indicate that a significant fraction of metastases and dangerous pre-malignant lesions can be identified through this strategy. Additionally, these findings indicate that other mutant nucleotide sequences, besides p53, which are associated or indicative of neoplasias, such as mutant proto oncogenes and tumor suppressor genes, would also be detectable.

A principal advantage of the method of this invention is that the PCR method of amplification can be used to detect one cancer cell in ten thousand cells in tissue margins of tumors. This high sensitivity is far superior to results obtained by the prior art methods of histologic examination. Moreover, this invention provides the diagnostician with an opportunity to screen tissue from patients determined to be at risk of developing tumors at an early stage before discernible tumors actually develop so that gene therapy and\or antisense therapy for such patients can commence at the time most likely to result in a successful outcome.

Although the invention has been described with reference to the presently preferred embodiment, it should be understood that various modifications can be made without departing from the spirit of the invention.

SEQUENCE ID LISTING

SEQUENCE ID NO. 1–2 are nucleotide sequences to which oligonucleotide primers for sequences flanking p53 mutations in exons 5–6, hybridize.

SEQUENCE ID NO. 3–4 are nucleotide sequences to which oligonucleotide primers for sequences flanking p53 mutations in exons 7–8, hybridize.

SEQUENCE ID NO. 5–8 are nucleotide sequences for primers which hybridize to flanking sequences of p53 mutations.

SEQUENCE ID NO. 9–11 are nucleotide sequences for mutant nucleotides in p53 at codons 273, 278, and 281, respectively.

SEQUENCE ID NO. 12 is the nucleotide sequence for a portion of the wild type p53.

SEQUENCE ID NO. 13 is the nucleotide sequence for a primer 4S for amplification of exons 5–9 of p53.

SEQUENCE ID NO. 14 is the nucleotide sequence for a primer 9AS for amplification of exons 5–9 of p53.

SEQUENCE ID NO. 15–73 are the nucleotide sequences for oligomers which are used to identify mutations in p53 which are associated with head and neck tumors.

SEQUENCE ID NO. 74–75 are the nucleotide sequences for mutant specific probes for codons 278 and 281 of p53, respectively.

SEQUENCE ID NO. 76–79 are the nucleotide sequences for primers used to amplify a 1.8 kb segment of the p53 gene encompassing exons 58.

SEQUENCE ID NO. 80–82 are the nucleotide sequences for probes for detection of p53 mutations.

I claim:

1. A method for detecting the presence of a mammalian target nucleic acid which contributes to the etiology of a neoplasm, in a tissue specimen, wherein the specimen is external to a primary neoplasm and the specimen does not exibit morphological charactersics indicative of neoplastic pathology, and the target nucleic acid is present in the primary neoplasm and the specimen, the specimen being selected from the group consisting of a tumor margin, a regional lymph node, chyle and blood the method comprising amplifying the nucleic acid present in the specimen by means of oligonucleotides that hybridize to the flanking regions of the target nucleic acid, wherein the nucleotide sequence of the flog region to which the oligonucleotide hybridizes is selected from the group of sequences consisting of:
    a) 5'-AAGTCAGGGCACAAGTGAATTCCTAC-3', (SEQUENCE ID NO. 1);
    b) 5'-AAGGGTGGTTGTCAGTGGAATTCGATG-3' (SEQUENCE ID NO. 2);
    c) 5'-GAGGCCAGTGCGCCTTGGAATTCCTAC-3' (SEQUENCE ID. NO. 3);
    d) 5'-GCGGTGGAGGAGACGAAGAATTCAGT-3' (SEQUENCE ID. NO. 4); and
    e) sequences complementary to a) through d) and detecting the presence of the target nucleic acid.

2. The method of claim 1, wherein the oligonucleotide is selected from the group of sequences consisting of:
    a) 5'-TTCACTTGTGCCCTGACTT-3' (SEQUENCE ID NO. 5);
    b) 5'-CCACTGACAACCACCCTT-3' (SEQUENCE ID NO. 7);
    c) 5'-CCAAGGCGCACTGGCCTC-3' (SEQUENCE ID NO. 8); and
    d) sequences complementary to sequence a) through d).

3. A method for detecting the presence of a mutated mammalian target nucleic acid in a tissue specimen, wherein the specimen is external to a primary neoplasm and the specimen does not exhibit morphological characteristics indicative of neoplastic pathology, and the target nucleic acid is present in the primary neoplasm and the specimen, the specimen being selected from the group consisting of a tumor margin, a regional lymph node, chyle and blood the method comprising amplifying the nucleic acid present in the specimen by means of oligonucleotides that hybridize to the target nucleic acid, wherein the nucleotide sequence of the target nucleic acid to which the oligonucleotide hybridizes is selected from the group of sequences consisting of:

a) 5'-CACAAACATGCACCTCAA-3' (SEQUENCE ID NO. 9);

b) 5'-TCTCCCAGTACAGGCACA-3' (SEQUENCE ID NO. 10);

c) 5'-TGCGCCGGGCCTCTCCCA-3' (SEQUENCE ID NO. 11);

d) 5'-CCGGTTCATGGCGCCCAT-3' (SEQUCE ID NO. 12); and e) sequences complementary to a) through d) and detecting the presence of the target nucleic acid.

4. The method of claim 3, wherein the oligonucleotide is selected from the group of sequences consisting of a) 5'-TTGAGGTGCATGTTTGTG-3' (SEQUENCE ID NO. 57);

b) 5'-TGGGAGAGGCCGGCGCA-3' (SEQUENCE ID NO. 80);

c) 5'-ATGGGCGCCATGAACCGG-3' (SEQUENCE ID NO. 81);

d) 5'-TGTGCCTGTACTGGGAGA-3' (SEQUENCE ID NO. 82); and e) sequences complementary to a) through d).

5. An isolated polynucleotide having a mutation present at p53 codons selected from the group consisting of 180, 187, 193 and 306.

6. The polynucleotide of claim 5, wherein the mutation is selected from the group consisting of:

180 GAG to TAG;

187 GGT to GAT;

193 CAT to CGT; and

306 CGT to TGA.

7. The polynucleotide of claim 5, wherein the polynucleotide is from a head or neck tumor.

8. A kit for the detection of a mammalian target nucleic acid which contributes to the etiology of a neoplasm from a tissue specimen wherein the specimen is external to a primary neoplasm and the specimen does not exhibit morphological characteristics indicative of neoplastic pathology and the mammalian target nucleic acid is present in the primary neoplasm and the specimen, the kit comprising carrier means being compartmentalized to receive therein one or more containers comprising a container containing a hybridization probe wherein the hybridization probe is selected from the group consisting of SEQ ID Nos:5, 6, 7, 8, 57, 80, 81, and 82, which hybridizes to the mammalian target nucleic acid.

9. The kit of claim 8, wherein the specimen is tumor margin tissue or a regional lymph node.

10. The kit of claim 8, further comprising a container containing an oligonucleotide primer for amplification of the target nucleic acid.

11. The kit of claim 8, wherein the probe contains a reporter-means.

12. The kit of claim 8, wherein the target nucleic acid is a mutant gene.

13. A method for detecting the presence of a mammalian target nucleic acid which contributes to the etiology of a neoplasm, in a tissue specimen, wherein the specimen is external to a primary neoplasm and the target nucleic acid is present in the primary neoplasm and the specimen, the specimen being selected from the group consisting of a tumor margin, a regional lymph node, chyle and blood, the method comprising extracting the nucleic acid present in the specimen and detecting the presence of the target nucleic acid; wherein the target nucleic acid is amplified before detecting;

wherein the amplification is by means of oligonucleotides that hybridize to the flanking regions of the target nucleic acid; and wherein the nucleotide sequence of the flanking region to which the oligonucleotide hybridizes is selected from the group of sequences consisting of:

a) 5'-AAGTCAGGGCACAAGTGAATTCCTAC-3', (SEQUENCE ID NO. 1);

b) 5'-AAGGGTGGTTGTCAGTGGAATTCGATG-3' (SEQUENCE ID NO. 2);

c) 5'-GAGGCCAGTGCGCCTTGGAATTCCTAC-3' (SEQUENCE ID. NO. 3); and d) 5'-GCGGTGGAGGAGACGAAGAATTCAGT-3' (SEQUENCE ID. NO. 4) and detecting the presence of the target nucleic acid.

14. The method of claim 13, wherein the oligonucleotide is selected from the group of sequences consisting of a) 5'-TTCACTTGTGCCCTGACTT-3' (SEQUENCE ID NO. 5);

b) 5'-CCACTGACAACCACCCTT-3' (SEQUENCE ID NO. 7); and c) 5'-CCAAGGCGCACTGGCCTC-3' (SEQUENCE ID NO. 8).

15. The method of claim 13, wherein the target nucleic acid is detected using a nucleotide hybridization probe specific for the target nucleic acid; and wherein the target nucleic acid to which the nucleotide hybridization probe hybridizes is selected from the group of sequences consisting of:

a) 5'-CACAAACATGCACCTCAA-3' (SEQUENCE ID NO. 9);

b) 5?-TCTCCCAGTACAGGCACA-3' (SEQUENCE ID NO. 10);

c) 5'-TGCGCCGGCCTCTCCCA-3' (SEQUENCE ID NO. 11); and d) 5'-CCGGTTCATGGCGCCCAT-3' (SEQUENCE ID NO. 12).

16. The method of claim 15, wherein the nucleotide hybridization probe is selected from the group of sequences consisting of a) 5'-TTGAGGTGCATGTTTGTG-3' (SEQUENCE ID NO. 57);

b) 5'-TGGGAGAGGCCGGCGCA-3' (SEQUENCE ID NO. 80);

c) 5'-ATGGGCGCCATGAACCGG-3' (SEQUENCE ID NO. 81); and d) 5'-TGTGCCTGTACTGGGAGA-3' (SEQUENCE ID NO. 82).

17. A kit for the detection of a mammalian target nucleic acid which contributes to the etiology of a neoplasm from a tissue specimen wherein the specimen is external to a primary neoplasm and the specimen does not exhibit morphological characteristics indicative of neoplastic pathology and the mammalian target nucleic acid is present in the primary neoplasm and the specimen, the kit comprising carrier means being compartmentalized to receive therein one or more containers comprising a container containing at least one oligonucleotide, wherein the nucleotide sequence of the target nucleic acid to which the oligonucleotide hybridizes is selected from the group of sequences consisting of:

a) 5'-AAGTCAGGGCACAAGTGAATTCCTAC-3', (SEQUENCE ID NO. 1);
b) 5'-AAGGGTGGTTGTCAGTGGAATTCGATG-3' (SEQUENCE ID NO. 2);
c) 5'-GAGGCCAGTGCGCCTTGGAATTCCTAC-3' (SEQUENCE ID. NO. 3);
d) 5'-GCGGTGGAGGAGACGAAGAATTCAGT-3' (SEQUENCE ID. NO. 4);
e) 5'-CACAAACATGCACCTCAA-3' (SEQUENCE ID NO. 9);
f) 5'-TCTCCCAGTACAGGCACA-3' (SEQUENCE ID NO. 10);
g) 5'-TGCGCCGGCCTCTCCCA-3' (SEQUENCE ID NO. 11); and
h) 5'-CCGGTTCATGGCGCCCAT-3' (SEQUENCE ID NO. 12).

18. The kit of claim 17, wherein the specimen is tumor margin tissue or a regional lymph node.

19. The kit of claim 17, wherein the probe contains a reporter-means.

20. The kit of claim 17, wherein the target nucleic acid is a mutant gene.

* * * * *